US012731694B2

(12) United States Patent
Kasmann et al.

(10) Patent No.: US 12,731,694 B2
(45) Date of Patent: Sep. 8, 2026

(54) SYSTEMS AND METHODS FOR AUTOMATED IDENTIFICATION AND LINKING OF DOMAIN-SPECIFIC CODING

(71) Applicant: Health Language, Inc., Denver, CO (US)

(72) Inventors: Jeremy John Kasmann, Evergreen, CO (US); Christopher Stanley Funk, Highlands Ranch, CO (US)

(73) Assignee: Health Language, Inc., Denver, CO (US)

( * ) Notice: Subject to any disclaimer, the term of this patent is extended or adjusted under 35 U.S.C. 154(b) by 0 days.

(21) Appl. No.: 18/941,342

(22) Filed: Nov. 8, 2024

(65) Prior Publication Data

US 2026/0134999 A1 May 14, 2026

Related U.S. Application Data

(60) Provisional application No. 63/597,825, filed on Nov. 10, 2023.

(51) Int. Cl.
*G16H 50/30* (2018.01)

(52) U.S. Cl.
CPC .................................. *G16H 50/30* (2018.01)

(58) Field of Classification Search
CPC ...................................................... G16H 50/30
See application file for complete search history.

(56) References Cited

U.S. PATENT DOCUMENTS 6,665,732 B1 * 12/2003 Garofalakis ............ H04L 67/61 709/233
10,489,502 B2 * 11/2019 Priestas .................. G06F 40/30
10,997,405 B1 * 5/2021 Lam ....................... G06N 3/084
11,074,412 B1 * 7/2021 Leeman-Munk ..... G06F 40/284
11,238,332 B2 * 2/2022 Ainslie ................ G06N 3/0455
11,822,612 B2 * 11/2023 Jia .......................... G06N 3/044
11,861,314 B2 * 1/2024 Pruksachatkun ...... G16H 10/60

(Continued)

OTHER PUBLICATIONS

International Search Report and Written Opinion for corresponding International Patent Application No. PCT/US2024/055347 dated Jan. 16, 2025, 14 pages.

*Primary Examiner* — Michael I Ezewoko
(74) *Attorney, Agent, or Firm* — Morgan, Lewis & Bockius LLP

(57) ABSTRACT

Systems and methods for anthology document delineation and code extraction are disclosed. An anthology document associated with a domain is received and a trained multi-modal extraction model is implemented to identify individual encounter records within the anthology document. The trained multimodal extraction model receives at least two input types generated from the anthology document. For each individual encounter record, one or more resource data structures and one or more value set data structures are generated. The resource data structure is representative of an entity in the individual encounter record. A value set data structure includes at least one resource data structure, a code element including a code selected from a code library associated with the domain, and a linkage element. Instructions configured to display an interface including the anthology document, the code, and a visual element representative of the at least one linkage element are generated.

16 Claims, 15 Drawing Sheets

(56) References Cited

U.S. PATENT DOCUMENTS

| | | | | |
|---|---|---|---|---|
| 11,935,316 | B1 * | 3/2024 | Rangarajan | G06V 10/82 |
| 11,941,706 | B2 * | 3/2024 | Hurd | G06N 20/20 |
| 12,135,958 | B2 * | 11/2024 | Pandita | G06F 8/33 |
| 12,217,525 | B1 * | 2/2025 | Rangarajan | G06V 30/19173 |
| 12,277,608 | B2 * | 4/2025 | Hurd | G06Q 40/123 |
| 2002/0103834 | A1 | 8/2002 | Thompson et al. | |
| 2010/0293451 | A1 | 11/2010 | Carus | |
| 2015/0100341 | A1 | 4/2015 | Pecora | |
| 2016/0210426 | A1 * | 7/2016 | Robinson | G16H 70/60 |
| 2018/0046764 | A1 | 2/2018 | Katwala et al. | |
| 2019/0005012 | A1 | 1/2019 | Priestas et al. | |
| 2020/0097717 | A1 * | 3/2020 | Young | G06N 3/09 |
| 2021/0082062 | A1 * | 3/2021 | Hurd | G06Q 40/123 |
| 2023/0074189 | A1 * | 3/2023 | Herard | G06N 3/0455 |
| 2023/0122684 | A1 * | 4/2023 | Larson | G06V 10/774<br>382/159 |
| 2024/0161203 | A1 * | 5/2024 | Falandino | G06Q 10/06311 |
| 2024/0161204 | A1 * | 5/2024 | Bien | G06Q 40/08 |
| 2024/0161530 | A1 * | 5/2024 | Falandino | G06V 30/19107 |
| 2024/0212061 | A1 * | 6/2024 | Hurd | G06N 20/00 |
| 2025/0036562 | A1 * | 1/2025 | Goren | G06F 11/3684 |
| 2025/0077857 | A1 * | 3/2025 | Xu | G06N 3/08 |

* cited by examiner

Receive Anthology Document
202

Identify Individual Encounter Record(s)
204

Generate Encounter Resource Data Structure(s)
206

Generate Value Set Data Structure(s)
208

Generate Annotated Anthology Document
210

Receive Feedback Data
212

Update Machine Learning Model(s)
214

SYSTEMS AND METHODS FOR AUTOMATED IDENTIFICATION AND LINKING OF DOMAIN-SPECIFIC CODING

CROSS-REFERENCE TO RELATED APPLICATION

This application claims benefit of U.S. Provisional Application Ser. No. 63/597,825, filed Nov. 10, 2023, entitled "Systems and Methods for Automated Identification and Linking of Domain-Specific Coding," the disclosure of which is incorporated herein by reference in its entirety.

TECHNICAL FIELD

This application relates generally to generation and deployment of machine learning models, and more particularly, to machine learning models configured to provide clinical coding and corresponding interfaces.

BACKGROUND

Domain-specific code libraries provide classification of certain concepts or elements that are associated with the corresponding domain. For example, a medical domain may have one or more coding libraries designed to codify diagnoses, procedures, medications, etc. Current coding practices require manual association of codes within a library based on manual review of documents within the domain. Such review is time consuming and dependent on the expertise and precision of a coder performing the review. Coding may be used to classify domain concepts into domain-specific categories.

For example, certain medical guidelines require classification of a patient or population into a category corresponding to diagnoses, treatments, etc. associated with the patient or population. Risk adjustment is performed to ensure correct coding of medical records with respect to cohorts, diagnoses, etc. to ensure proper classification of the patient and/or population. Current risk adjustment includes a manual code review of medical records by highly skilled personnel to verify existing codes and identify missing codes. Current manual risk adjustment is a time intensive and error prone process.

SUMMARY

In various embodiments, a system including a non-transitory memory and a processor communicatively coupled to the non-transitory memory is disclosed. The processor is configured to read a set of instructions to receive an anthology document associated with a domain and implement a trained multimodal extraction model to identify one or more individual encounter records within the anthology document. The trained multimodal extraction model is configured to receive at least two input types generated from the anthology document. The processor is further configured to, for each of the one or more individual encounter records, generate one or more resource data structures representative of an entity in a selected one of the one or more individual encounter records and generate one or more value set data structures comprising at least one of the one or more resource data structures, at least one code element comprising a code selected from a code library associated with the domain, and at least one linkage element representative of a linkage between the entity of the at least one of the one or more resource data structures and the code element. The entity is identified by a trained natural language processing model. The processor is further configured to generate instructions configured to display an interface including the anthology document, the code, and a visual element representative of the at least one linkage element.

In various embodiments, a computer-implemented method is disclosed. The computer-implemented method includes steps of receiving an anthology document associated with a domain and implementing a trained multimodal extraction model to identify one or more individual encounter records within the anthology document. For each of the one or more individual encounter records, the computer-implemented method includes steps of generating one or more resource data structures comprising an annotation data element representative of an entity in a selected one of the one or more individual encounter records and generating one or more value set data structures comprising at least one of the one or more resource data structures, at least one code element comprising a code selected from a code library associated with the domain, and at least one linkage element representative of a linkage between the entity of the at least one of the one or more resource data structures and the code element. The entity is identified by a trained natural language processing model. The computer-implemented method includes a step of generating instructions configured to display an interface including the anthology document, the code, and a visual element representative of the at least one linkage element.

In various embodiments, a non-transitory computer readable medium having instructions stored thereon is disclosed. The instructions, when executed by at least one processor, cause at least one device to perform operations including receiving an anthology document associated with a domain and implementing a trained multimodal extraction model to identify one or more individual encounter records within the anthology document. The trained multimodal extraction model is configured to receive a text input and an image input and each of the text input and the image input are generated from the anthology document. The at least one device performs operations further including, for each of the one or more individual encounter records, generating one or more resource data structures comprising an annotation data element representative of an entity in a selected one of the one or more individual encounter records and generating one or more value set data structures comprising at least one of the one or more resource data structures, at least one code element comprising a code selected from a code library associated with the domain, and at least one linkage element representative of a linkage between the entity of the at least one of the one or more resource data structures and the code element. The entity is identified by a trained natural language processing model. The at least one device performs an operation further including generating instructions configured to display an interface including the anthology document, the code, and a visual element representative of the at least one linkage element.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
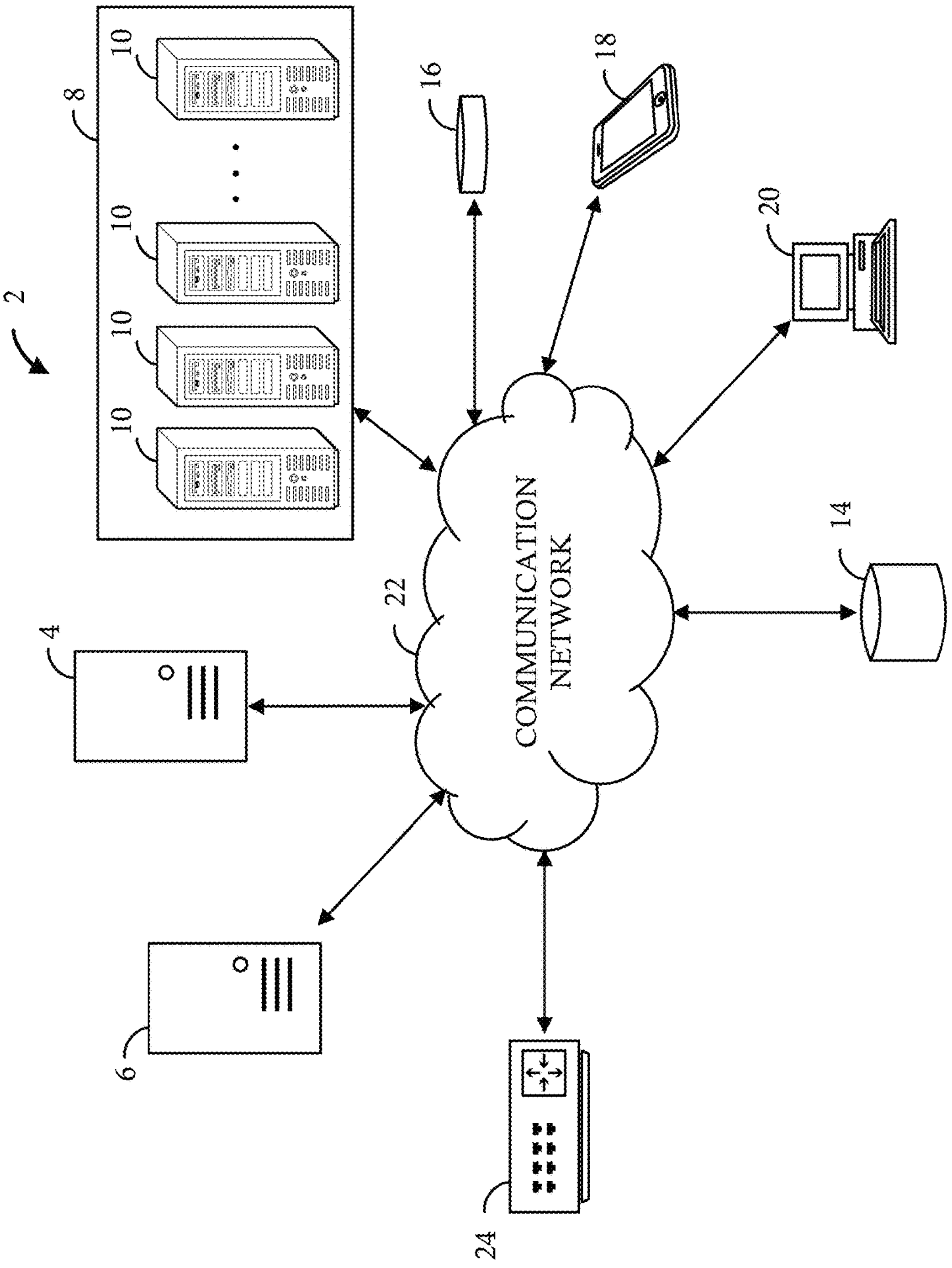
FIG. 1 illustrates a network environment configured to provide a machine learning based coding environment, in accordance with some embodiments.

This description of the exemplary embodiments is intended to be read in connection with the accompanying drawings, which are to be considered part of the entire written description. Terms concerning data connections, coupling and the like, such as "connected" and "interconnected," and/or "in signal communication with" refer to a relationship wherein systems or elements are electrically connected (e.g., wired, wireless) to one another either directly or indirectly through intervening systems, unless expressly described otherwise. The term "operatively coupled" is such a coupling or connection that allows the pertinent structures to operate as intended by virtue of that relationship.

In the following, various embodiments are described with respect to the claimed systems as well as with respect to the claimed methods. Features, advantages, or alternative embodiments herein may be assigned to the other claimed objects and vice versa. In other words, claims for the systems may be improved with features described or claimed in the context of the methods. In this case, the functional features of the method are embodied by objective units of the systems. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

Furthermore, in the following, various embodiments are described with respect to methods and systems for code extraction and review. In various embodiments, an anthology document associated with a domain is received and a trained multimodal extraction model is implemented to identify one or more individual encounter records within the anthology document. The trained multimodal extraction model is configured to receive at least two input types generated from the anthology document. For each of the one or more individual encounter records, one or more resource data structures representative of an entity in a selected one of the one or more individual encounter records is generated. One or more value set data structures comprising at least one of the one or more resource data structures, at least one code element comprising a code is selected from a code library associated with the domain and at least one linkage element representative of a linkage between the entity of the at least one of the one or more resource data structures and the code element is generated. The entity is identified by a trained natural language processing model. An interface is generated including the anthology document, the code, and a visual element representative of the at least one linkage element In some embodiments, systems, and methods for code extraction and review include one or more trained multimodal extraction models, natural language processing models, and/or other suitable machine learning models. The trained models may include one or more models, such as a trained multimodal model configured to receive two or more input types generated from an anthology document and generate a classification output for each page in the anthology document. The trained models may further include trained natural language processing models configured to extract terms or elements from each of the encounters or pages in the anthology document.

In general, a trained function mimics cognitive functions that humans associate with other human minds. In particular, by training based on training data the trained function is able to adapt to new circumstances and to detect and extrapolate patterns.

In general, parameters of a trained function may be adapted by means of training. In particular, a combination of supervised training, semi-supervised training, unsupervised training, reinforcement learning and/or active learning may be used. Furthermore, representation learning (an alternative term is "feature learning") may be used. In particular, the parameters of the trained functions may be adapted iteratively by several steps of training.

In some embodiments, a trained function may include a neural network, a support vector machine, a decision tree, a Bayesian network, a clustering network, Qlearning, genetic algorithms and/or association rules, and/or any other suitable artificial intelligence architecture. In some embodiments, a neural network may be a deep neural network, a convolutional neural network, a convolutional deep neural network, etc. Furthermore, a neural network may be an adversarial network, a deep adversarial network, a generative adversarial network, etc.

In various embodiments, neural networks which are trained (e.g., configured or adapted) to generate delineated individual encounter records, data structures, and/or coding linkages, are disclosed. A neural network trained to generate delineated individual encounter records may be referred to as a trained encounter generation model, a trained natural language processing model, etc. A trained natural language processing model may be configured to receive a set of input data, such as a document or collection of text, and generate outputs identifying various language elements within the documents, such as words, parts of speech, context, etc. In some embodiments, one or more trained natural language processing models are generated and deployed to assist in delineation of individual encounter records and/or generation of data structures including document data elements and code linkages.

FIG. 1 illustrates a network environment 2 configured to provide a machine learning based coding environment, in accordance with some embodiments. The network environment 2 includes a plurality of devices or systems configured to communicate over one or more network channels, illustrated as a network cloud 22. For example, in various embodiments, the network environment 2 may include, but is not limited to, a coding computing device 4, a web server 6, a cloud-based engine 8 including one or more processing devices 10, a database 14, and/or one or more user computing devices 16, 18, 20 operatively coupled over the network 22. The coding computing device 4, the web server 6, the processing device(s) 10, and/or the user computing devices 16, 18, 20 may each be a suitable computing device that includes any hardware or hardware and software combination for processing and handling information. For example, each computing device may include, but is not limited to, one or more processors, one or more field-programmable gate arrays (FPGAs), one or more application-specific integrated circuits (ASICs), one or more state machines, digital circuitry, and/or any other suitable circuitry. In addition, each computing device may transmit and receive data over the communication network 22.

In some embodiments, each of the coding computing device 4 and the processing device(s) 10 may be a computer, a workstation, a laptop, a server such as a cloud-based server, or any other suitable device. In some embodiments, each of the processing devices 10 is a server that includes one or more processing units, such as one or more graphical processing units (GPUs), one or more central processing units (CPUs), and/or one or more processing cores. Each processing device 10 may, in some embodiments, execute one or more virtual machines. In some embodiments, processing resources (e.g., capabilities) of the one or more processing devices 10 are offered as a cloud-based service (e.g., cloud computing). For example, the cloud-based engine 8 may offer computing and storage resources of the one or more processing devices 10 to the coding computing device 4.

In some embodiments, each of the user computing devices 16, 18, 20 may be a cellular phone, a smart phone, a tablet, a personal assistant device, a voice assistant device, a digital assistant, a laptop, a computer, or any other suitable device. In some embodiments, the web server 6 hosts one or more network environments, such as an e-commerce network environment. In some embodiments, the coding computing device 4, the processing devices 10, and/or the web server 6 are operated by the network environment provider, and the user computing devices 16, 18, 20 are operated by users of the network environment. In some embodiments, the processing devices 10 are operated by a third party (e.g., a cloud-computing provider).

Although FIG. 1 illustrates three user computing devices 16, 18, 20, the network environment 2 may include any number of user computing devices 16, 18, 20. Similarly, the network environment 2 may include any number of the coding computing device 4, the web server 6, the processing devices 10, and/or the databases 14. It will further be appreciated that additional systems, servers, storage mechanism, etc. may be included within the network environment 2. In addition, although embodiments are illustrated herein having individual, discrete systems, it will be appreciated that, in some embodiments, one or more systems may be combined into a single logical and/or physical system. For example, in various embodiments, one or more of the coding computing device 4, the web server 6, the database 14, the user computing devices 16, 18, 20, and/or a router 24 may be combined into a single logical and/or physical system. Similarly, although embodiments are illustrated having a single instance of each device or system, it will be appreciated that additional instances of a device may be implemented within the network environment 2. In some embodiments, two or more systems may be operated on shared hardware in which each system operates as a separate, discrete system utilizing the shared hardware, for example, according to one or more virtualization schemes.

The communication network 22 may be a WiFi® network, a cellular network such as a 3GPP® network, a Bluetooth® network, a satellite network, a wireless local area network (LAN), a network utilizing radio-frequency (RF) communication protocols, a Near Field Communication (NFC) network, a wireless Metropolitan Area Network (MAN) connecting multiple wireless LANs, a wide area network (WAN), or any other suitable network. The communication network 22 may provide access to, for example, the Internet.

Each of the user computing devices 16, 18, 20 may communicate with the web server 6 over the communication network 22. For example, each of the user computing devices 16, 18, 20 may be operable to view, access, and interact with a web application, such as a machine learning based coding application, hosted by the web server 6. The web server 6 may transmit user session data related to a user's activity (e.g., interactions) on the website. For example, a user may operate one of the user computing devices 16, 18, 20 to initiate a web browser that is directed to the web application hosted by the web server 6. The user may, via the web browser, perform various operations such as searching one or more databases or catalogs associated with the displayed web application, view item data for elements associated with and displayed on the web application, and click on interface elements presented via the web application, etc. The web application may capture these activities as user session data, and transmit the user session data to the coding computing device 4 over the communication network 22. The website may also allow the user to interact with one or more of interface elements to perform specific operations, such as selecting one or more elements for further processing.

In some embodiments, the coding computing device 4 may execute one or more models, processes, or algorithms, such as a machine learning model, deep learning model, statistical model, etc., to generate delineated encounter records and/or associate elements of delineated encounter records with one or more codes in a predetermined code library.

The coding computing device 4 is further operable to communicate with the database 14 over the communication network 22. For example, the coding computing device 4 may store data to, and read data from, the database 14. The database 14 may be a remote storage device, such as a cloud-based server, a disk (e.g., a hard disk), a memory device on another application server, a networked computer, or any other suitable remote storage. Although shown remote to the coding computing device 4, in some embodiments, the database 14 may be a local storage device, such as a hard drive, a non-volatile memory, or a USB stick. The coding computing device 4 may store interaction data received from the web server 6 in the database 14.

In some embodiments, the coding computing device 4 generates training data for a plurality of models (e.g., machine learning models, deep learning models, statistical models, algorithms) based on historical data, labeled data, etc. The coding computing device 4 and/or one or more of the processing devices 10 may train one or more models based on corresponding training data. The coding computing device 4 may store the models in a database, such as in the database 14 (e.g., a cloud storage database).

The models, when executed by the coding computing device 4, allow the coding computing device 4 to delineate individual encounter records within a corpus and/or associate elements within each of the individual encounter records with codes obtained from a predetermined code library. For example, the coding computing device 4 may obtain one or more models from the database 14. The coding computing device 4 may then receive, in real-time from the web server 6, an anthology document containing one or more encounter records. In response to receiving the anthology document, the coding computing device 4 may execute one or more models to delineate and/or extract individual encounter records in/from the anthology document and/or to associate identified elements of the individual encounter record(s) with one or more codes obtained from a predetermined code library.

In some embodiments, the coding computing device 4 assigns the models (or parts thereof) for execution to one or more processing devices 10. For example, each model may be assigned to a virtual machine hosted by a processing device 10. The virtual machine may cause the models or parts thereof to execute on one or more processing units such as GPUs. In some embodiments, the virtual machines assign each model (or part thereof) among a plurality of processing units. Based on the output of the models, coding computing device 4 may generate one or more data structures, such as, for example, one or more resource data structures, one or more value set data structures, etc.

Figure 2:
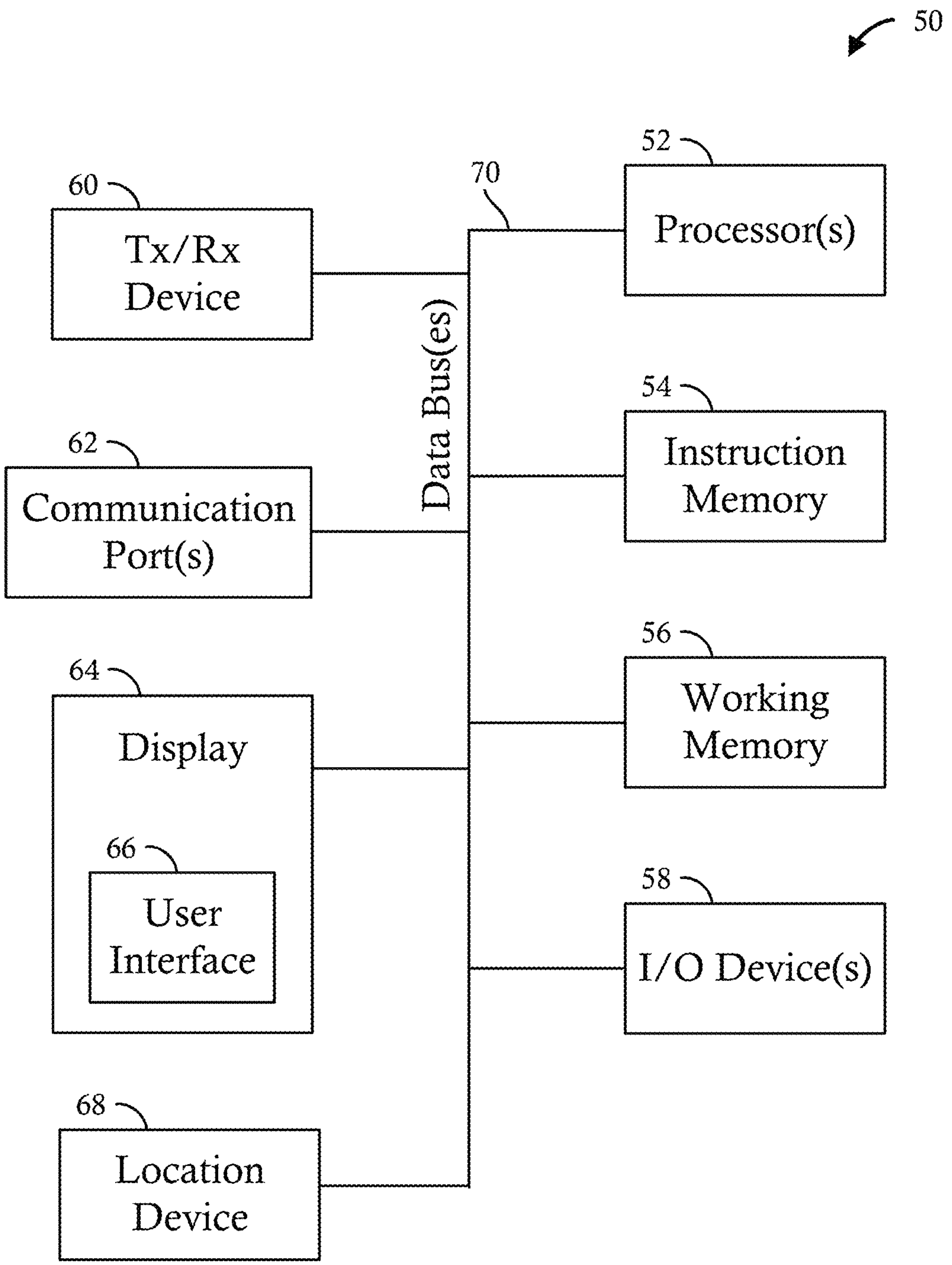
FIG. 2 illustrates a computer system configured to implement one or more processes, in accordance with some embodiments.

FIG. 2 illustrates a block diagram of a computing device 50, in accordance with some embodiments. In some embodiments, each of the coding computing device 4, the web server 6, the one or more processing devices 10, and/or the user computing devices 16, 18, 20 in FIG. 1 may include the features shown in FIG. 2. Although FIG. 2 is described with respect to certain components shown therein, it will be appreciated that the elements of the computing device 50 may be combined, omitted, and/or replicated. In addition, it will be appreciated that additional elements other than those illustrated in FIG. 2 may be added to the computing device.

As shown in FIG. 2, the computing device 50 may include one or more processors 52, an instruction memory 54, a working memory 56, one or more input/output devices 58, a transceiver 60, one or more communication ports 62, a display 64 with a user interface 66, and an optional location device 68, all operatively coupled to one or more data buses 70. The data buses 70 allow for communication among the various components. The data buses 70 may include wired, or wireless, communication channels.

The one or more processors 52 may include any processing circuitry operable to control operations of the computing device 50. In some embodiments, the one or more processors 52 include one or more distinct processors, each having one or more cores (e.g., processing circuits). Each of the distinct processors may have the same or different structure. The one or more processors 52 may include one or more central processing units (CPUs), one or more graphics processing units (GPUs), application specific integrated circuits (ASICs), digital signal processors (DSPs), a chip multiprocessor (CMP), a network processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The one or more processors 52 may also be implemented by a controller, a microcontroller, an application specific integrated circuit (ASIC), a field programmable gate array (FPGA), a programmable logic device (PLD), etc.

In some embodiments, the one or more processors 52 are configured to implement an operating system (OS) and/or various applications. Examples of an OS include, for example, operating systems generally known under various trade names such as Apple macOS™, Microsoft Windows™, Android™, Linux™, and/or any other proprietary or open-source OS. Examples of applications include, for example, network applications, local applications, data input/output applications, user interaction applications, etc.

The instruction memory 54 may store instructions that are accessed (e.g., read) and executed by at least one of the one or more processors 52. For example, the instruction memory 54 may be a non-transitory, computer-readable storage medium such as a read-only memory (ROM), an electrically erasable programmable read-only memory (EEPROM), flash memory (e.g. NOR and/or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, a removable disk, CD-ROM, any non-volatile memory, or any other suitable memory. The one or more processors 52 may be configured to perform a certain function or operation by executing code, stored on the instruction memory 54, embodying the function or operation. For example, the one or more processors 52 may be configured to execute code stored in the instruction memory 54 to perform one or more of any function, method, or operation disclosed herein.

Additionally, the one or more processors 52 may store data to, and read data from, the working memory 56. For example, the one or more processors 52 may store a working set of instructions to the working memory 56, such as instructions loaded from the instruction memory 54. The one or more processors 52 may also use the working memory 56 to store dynamic data created during one or more operations. The working memory 56 may include, for example, random access memory (RAM) such as a static random access memory (SRAM) or dynamic random access memory (DRAM), Double-Data-Rate DRAM (DDR-RAM), synchronous DRAM (SDRAM), an EEPROM, flash memory (e.g. NOR and/or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, a removable disk, CD-ROM, any non-volatile memory, or any other suitable memory. Although embodiments are illustrated herein including separate instruction memory 54 and working memory 56, it will be appreciated that the computing device 50 may include a single memory unit configured to operate as both instruction memory and working memory. Further, although embodiments are discussed herein including non-volatile memory, it will be appreciated that computing device 50 may include volatile memory components in addition to at least one non-volatile memory component.

In some embodiments, the instruction memory 54 and/or the working memory 56 includes an instruction set, in the form of a file for executing various methods, such as methods for code extraction and review, as described herein. The instruction set may be stored in any acceptable form of machine-readable instructions, including source code or various appropriate programming languages. Some examples of programming languages that may be used to store the instruction set include, but are not limited to: Java, Javascript, C, C++, C#, Python, Objective-C, Visual Basic, .NET, HTML, CSS, SQL, NoSQL, Rust, Perl, etc. In some embodiments a compiler or interpreter is configured to convert the instruction set into machine executable code for execution by the one or more processors 52.

The input-output devices 58 may include any suitable device that allows for data input or output. For example, the input-output devices 58 may include one or more of a keyboard, a touchpad, a mouse, a stylus, a touchscreen, a physical button, a speaker, a microphone, a keypad, a click wheel, a motion sensor, a camera, and/or any other suitable input or output device.

The transceiver 60 and/or the communication port(s) 62 allow for communication with a network, such as the communication network 22 of FIG. 1. For example, if the communication network 22 of FIG. 1 is a cellular network, the transceiver 60 is configured to allow communications with the cellular network. In some embodiments, the transceiver 60 is selected based on the type of the communication network 22 the computing device 50 will be operating in. The one or more processors 52 are operable to receive data from, or send data to, a network, such as the communication network 22 of FIG. 1, via the transceiver 60.

The communication port(s) 62 may include any suitable hardware, software, and/or combination of hardware and software that is capable of coupling the computing device 50 to one or more networks and/or additional devices. The communication port(s) 62 may be arranged to operate with any suitable technique for controlling information signals using a desired set of communications protocols, services, or operating procedures. The communication port(s) 62 may include the appropriate physical connectors to connect with a corresponding communications medium, whether wired or wireless, for example, a serial port such as a universal asynchronous receiver/transmitter (UART) connection, a Universal Serial Bus (USB) connection, or any other suitable communication port or connection. In some embodiments, the communication port(s) 62 allows for the programming of executable instructions in the instruction memory 54. In some embodiments, the communication port(s) 62 allow for the transfer (e.g., uploading or downloading) of data, such as machine learning model training data.

In some embodiments, the communication port(s) 62 are configured to couple the computing device 50 to a network. The network may include local area networks (LAN) as well as wide area networks (WAN) including without limitation Internet, wired channels, wireless channels, communication devices including telephones, computers, wire, radio, optical and/or other electromagnetic channels, and combinations thereof, including other devices and/or components capable of/associated with communicating data. For example, the communication environments may include in-body communications, various devices, and various modes of communications such as wireless communications, wired communications, and combinations of the same.

In some embodiments, the transceiver 60 and/or the communication port(s) 62 are configured to utilize one or more communication protocols. Examples of wired protocols may include, but are not limited to, Universal Serial Bus (USB) communication, RS-232, RS-422, RS-423, RS-485 serial protocols, FireWire, Ethernet, Fibre Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, etc. Examples of wireless protocols may include, but are not limited to, the Institute of Electrical and Electronics Engineers (IEEE) 802.xx series of protocols, such as IEEE 802.11a/b/g/n/ac/ag/ax/be, IEEE 802.16, IEEE 802.20, GSM cellular radiotelephone system protocols with GPRS, CDMA cellular radiotelephone communication systems with 1×RTT, EDGE systems, EV-DO systems, EV-DV systems, HSDPA systems, Wi-Fi Legacy, Wi-Fi 1/2/3/4/5/6/6E, wireless personal area network (PAN) protocols, Bluetooth Specification versions 5.0, 6, 7, legacy Bluetooth protocols, passive or active radio-frequency identification (RFID) protocols, Ultra-Wide Band (UWB), Digital Office (DO), Digital Home, Trusted Platform Module (TPM), ZigBee, etc.

The display 64 may be any suitable display, and may display the user interface 66. The user interfaces 66 may enable user interaction with generated data structures, such as resource data structures, value set data structures, etc. For example, the user interface 66 may be a user interface for an application of a network environment operator that allows a user to view and interact with the operator's website. In some embodiments, a user may interact with the user interface 66 by engaging the input-output devices 58. In some embodiments, the display 64 may be a touchscreen, where the user interface 66 is displayed on the touchscreen.

The display 64 may include a screen such as, for example, a Liquid Crystal Display (LCD) screen, a light-emitting diode (LED) screen, an organic LED (OLED) screen, a movable display, a projection, etc. In some embodiments, the display 64 may include a coder/decoder, also known as Codecs, to convert digital media data into analog signals. For example, the visual peripheral output device may include video Codecs, audio Codecs, or any other suitable type of Codec.

The optional location device 68 may be communicatively coupled to a location network and operable to receive position data from the location network. For example, in some embodiments, the location device 68 includes a GPS device configured to receive position data identifying a latitude and longitude from one or more satellites of a GPS constellation. As another example, in some embodiments, the location device 68 is a cellular device configured to receive location data from one or more localized cellular towers. Based on the position data, the computing device 50 may determine a local geographical area (e.g., town, city, state) of its position.

In some embodiments, the computing device 50 is configured to implement one or more modules or engines, each of which is constructed, programmed, configured, or otherwise adapted, to autonomously carry out a function or set of functions. A module/engine may include a component or arrangement of components implemented using hardware, such as by an application specific integrated circuit (ASIC) or field-programmable gate array (FPGA), for example, or as a combination of hardware and software, such as by a microprocessor system and a set of program instructions that adapt the module/engine to implement the particular functionality, which (while being executed) transform the microprocessor system into a special-purpose device. A module/engine may also be implemented as a combination of the two, with certain functions facilitated by hardware alone, and other functions facilitated by a combination of hardware and software. In certain implementations, at least a portion, and in some cases, all, of a module/engine may be executed on the processor(s) of one or more computing platforms that are made up of hardware (e.g., one or more processors, data storage devices such as memory or drive storage, input/output facilities such as network interface devices, video devices, keyboard, mouse or touchscreen devices) that execute an operating system, system programs, and application programs, while also implementing the engine using multitasking, multithreading, distributed (e.g., cluster, peer-peer, cloud) processing where appropriate, or other such techniques. Accordingly, each module/engine may be realized in a variety of physically realizable configurations, and should generally not be limited to any particular implementation exemplified herein, unless such limitations are expressly called out. In addition, a module/engine may itself be composed of more than one sub-modules or sub-engines, each of which may be regarded as a module/engine in its own right. Moreover, in the embodiments described herein, each of the various modules/engines corresponds to a defined autonomous functionality; however, it should be understood that in other contemplated embodiments, each functionality may be distributed to more than one module/engine. Likewise, in other contemplated embodiments, multiple defined functionalities may be implemented by a single module/engine that performs those multiple functions, possibly alongside other functions, or distributed differently among a set of modules/engines.

Figure 3:
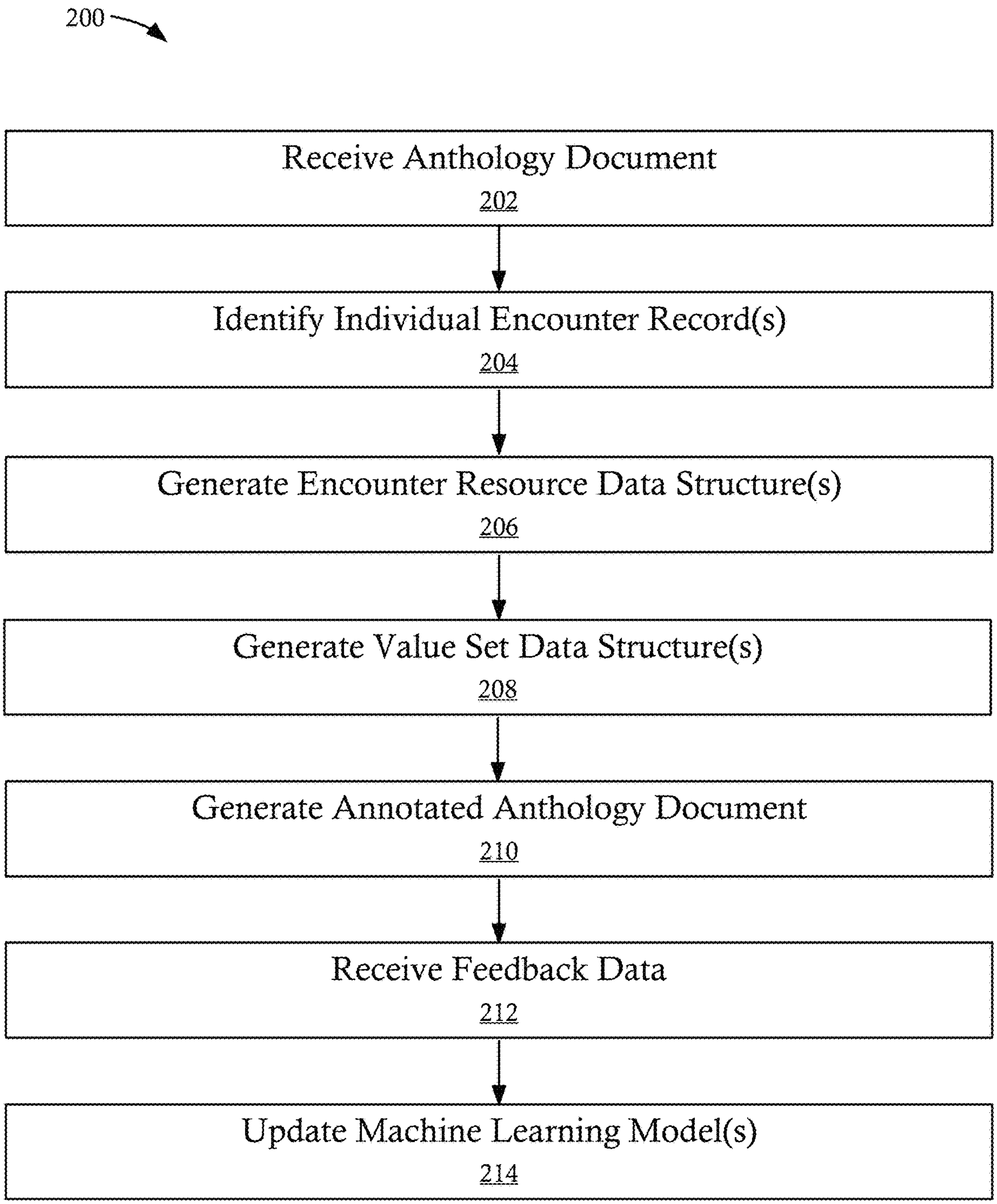
FIG. 3 is a flowchart illustrating a code extraction and review method, in accordance with some embodiments.
Figure 4:
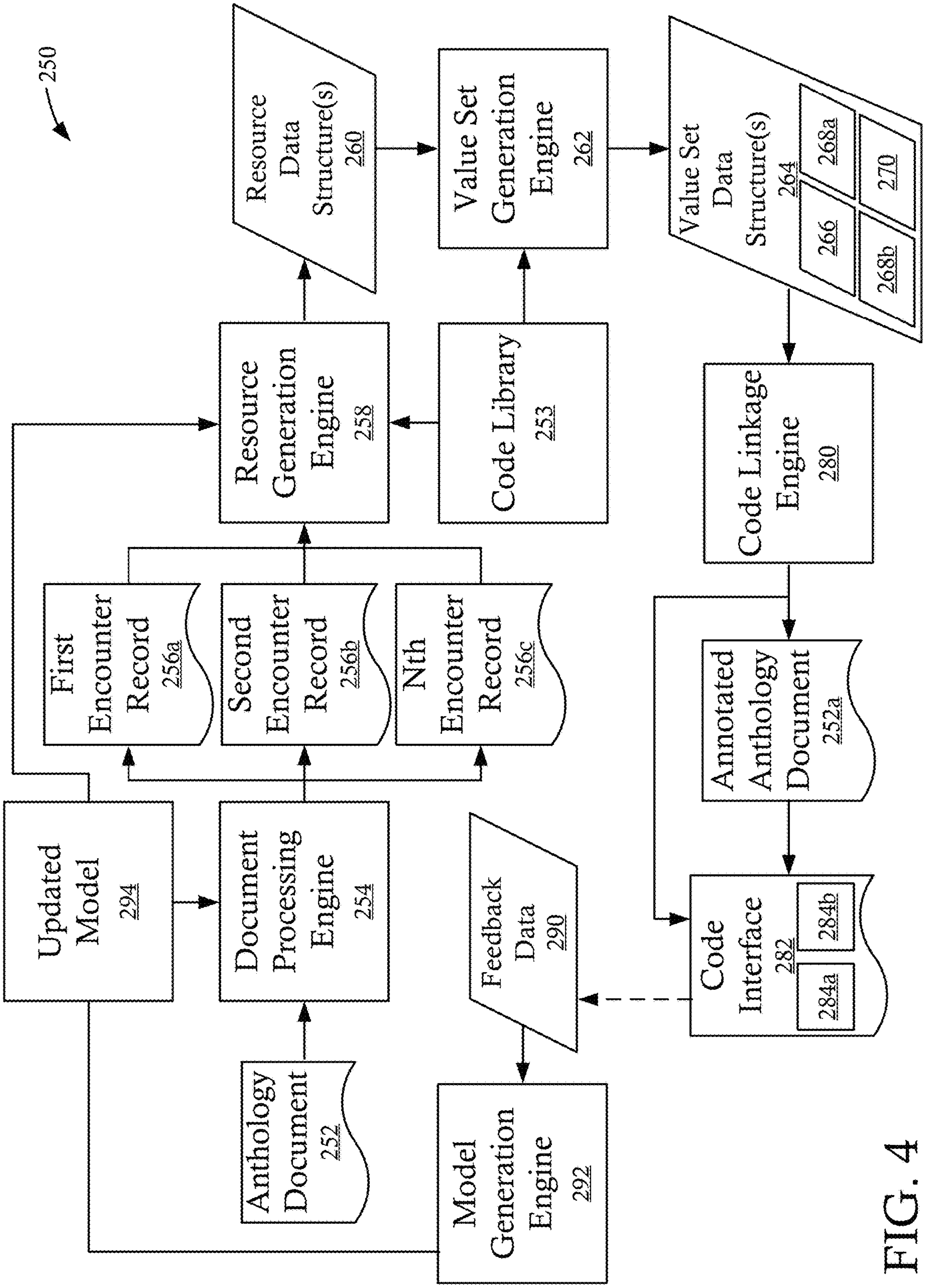
FIG. 4 is a process flow illustrating various steps of the code extraction and review method of FIG. 3, in accordance with some embodiments.

FIG. 3 is a flowchart illustrating a code extraction and review method 200, in accordance with some embodiments. FIG. 4 is a process flow 250 illustrating various steps of the code extraction and review method 200, in accordance with some embodiments. At step 202, an anthology document 252 including data representative of one or more encounters is received. An encounter may include an interaction and/or other event recorded in the anthology document 252. For example, in some embodiments, the anthology document 252 includes a medical file (e.g., a patient chart) that documents encounters including, but not limited to, office visits, medical testing and/or results (e.g., lab testing, diagnostic testing), progress notes, treatment records, medication profiles, consent forms, provider reports, care plans, etc. The anthology document 252 may include any suitable document format and/or any suitable file format. For example, in some embodiments, the anthology document 252 includes a medical chart in a portable document format (PDF) file format. In some embodiments, the anthology document 252 is in and/or retrieved from a database, such as the database 14*a*.

The anthology document 252 is associated with one or more domains having one or more code libraries 253 associated therewith. The one or more code libraries 253 provide codification of domain-specific concepts, elements, procedures, activities, etc. For example, in some embodiments, the anthology document 252 includes a medical file associated with a medical domain having one or more code libraries 253 associated therewith that codify elements associated with the medical domain. For example, code libraries associated with a medical domain may include, but are not limited to, an International Classification of Disease (ICD) code set (e.g., ICD-9, ICD-10, ICD-11, ICD-10 Clinical Modification (CM) (ICD-10-CM), ICD-10 Procedure Coding System (PCS) (ICD-10-PCS)), Current Procedural Terminology (CPT) Procedure Codes, Healthcare Common Procedure Coding System (HCPCS) codes, ABC codes, etc. Although certain embodiments are discussed herein, it will be appreciated that the disclosed systems and methods are applicable to any suitable anthology document 252, provided in any suitable format, and applicable to any domain having at least one code library 253 associated therewith.

At step 204, the anthology document 252 is processed to identify individual encounter records 256*a*-256*c* (collectively "individual encounter records 256") within the anthology document 252. Each of the identified individual encounter records 256 includes a set of selected (e.g., delineated, extracted) pages of the anthology document 252 that are associated with and/or document a single event (e.g., interaction, test, procedure). As one non-limiting example, in some embodiments, the anthology document 252 may include a medical file consisting of multiple events or note types, such as one or more office visit records, medical testing and/or results (e.g., lab testing, diagnostic testing), progress notes, treatment records, medication profiles, consent forms, provider reports, care plans, etc. The pages of the anthology document 252 corresponding to each individual event may be delineated and/or extracted as an individual encounter record 256*a*-256*c*.

Figure 5:
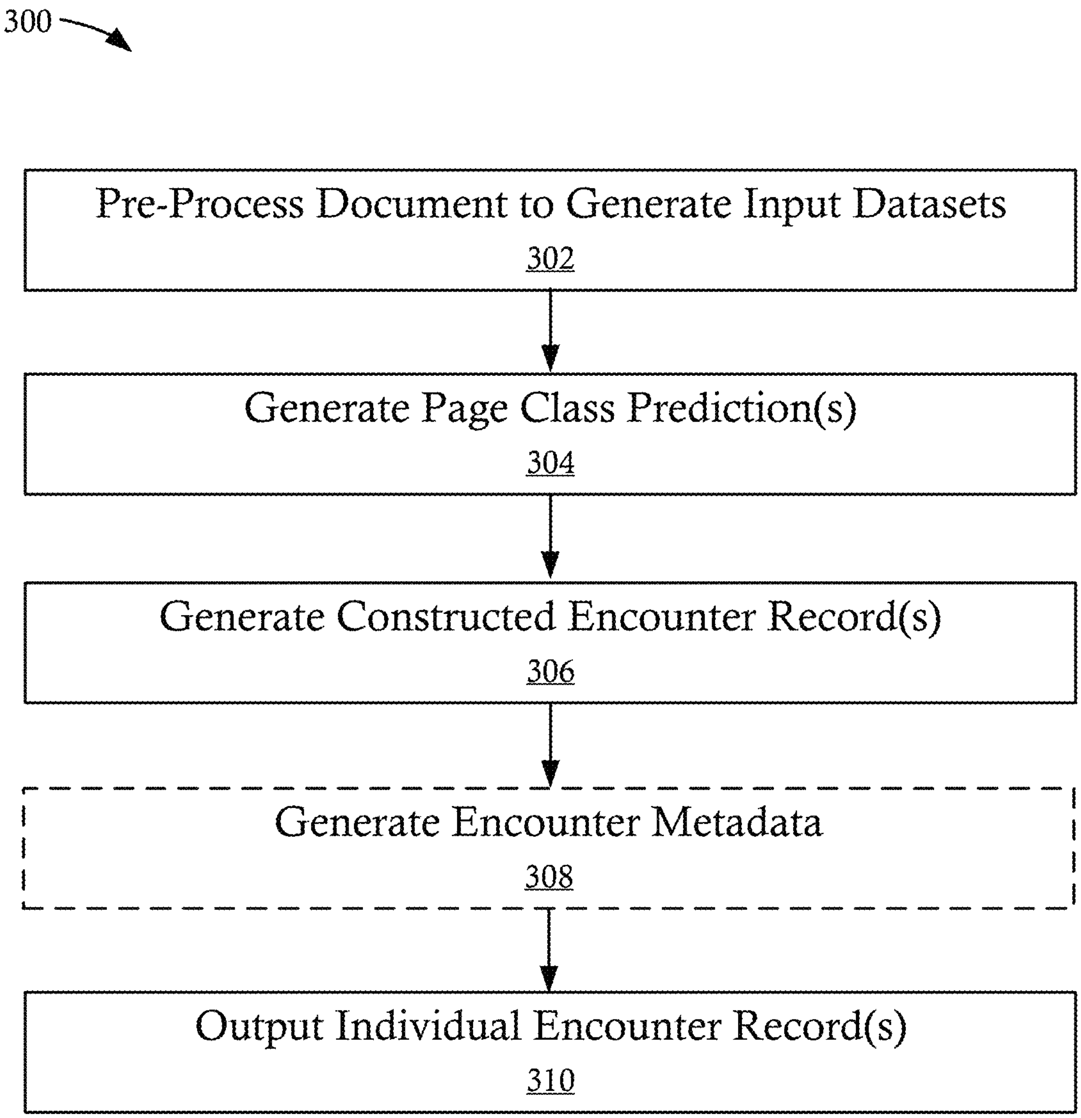
FIG. 5 is a flowchart illustrating an encounter construction method, in accordance with some embodiments.
Figure 6:
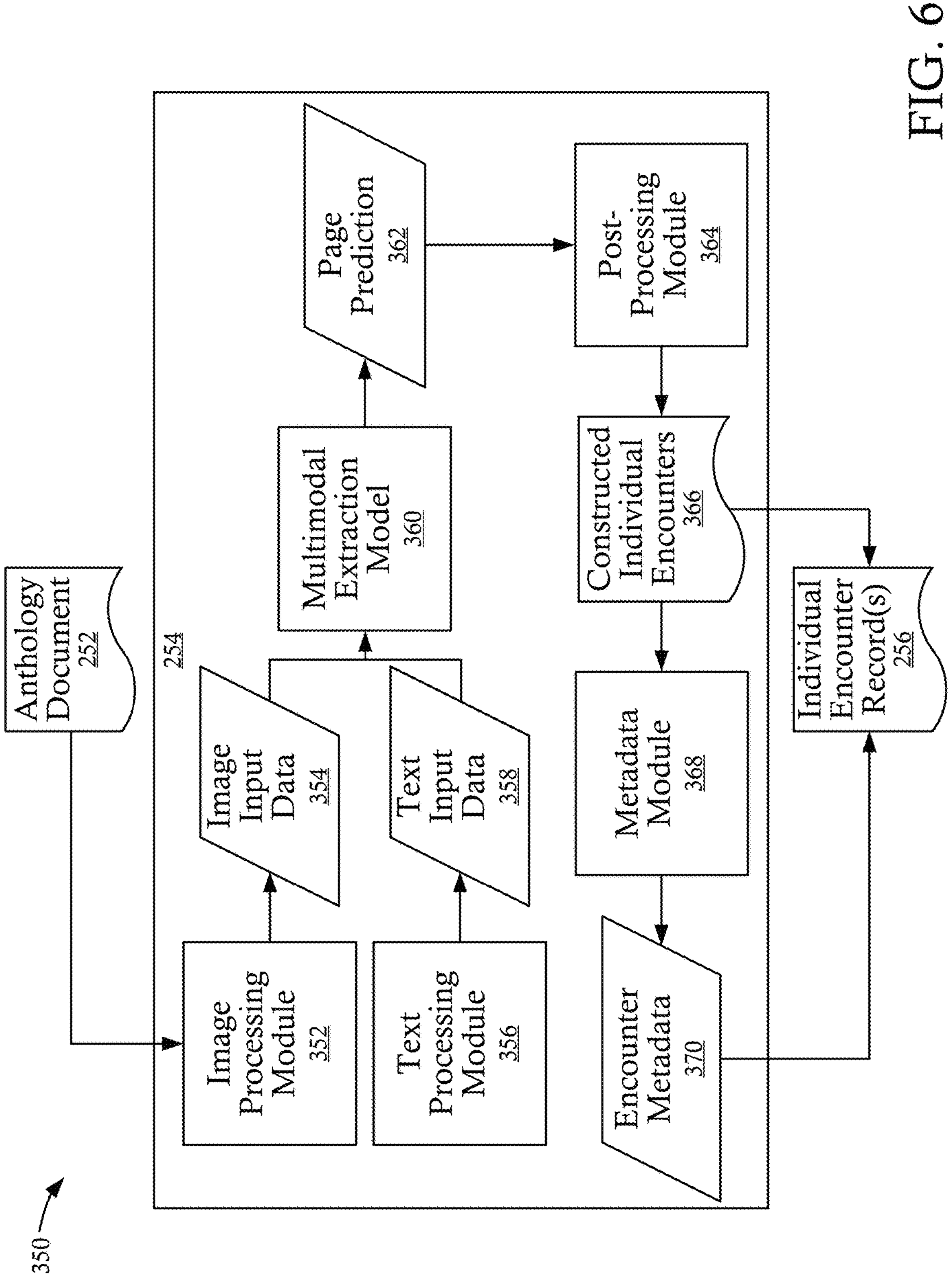
FIG. 6 is a process flow illustrating various steps of the encounter construction method of FIG. 5, in accordance with some embodiments.

FIG. 5 is a flowchart illustrating an encounter construction method 300, in accordance with some embodiments. FIG. 6 is a process flow 350 illustrating various steps of the encounter construction method 300, in accordance with some embodiments. The encounter construction method 300 may be implemented by any suitable engine, system, method, etc., such as a document processing engine 254. At step 302, the anthology document 252 is pre-processed to generate one or more input datasets 354, 358. For example, in some embodiments, the document processing engine 254 includes an image processing module 352 configured to extract and/or generate images from the anthology document 252 to generate image input data 354 and a text processing module 356 configured to extract text input data 358.

In some embodiments, the image processing module 352 is configured generate individual image data for each page in the anthology document 252. For example, the image processing module 352 may extract each page in the anthology document 252 and generate a separate image file (e.g., a file in an image format such as, for example, multiple tag image file format (TIFF) files) for each page. The image processing module 352 may apply image pre-processing techniques to the extracted and/or generated individual image data to generate the image input data 354. The image processing module 352 may be configured to apply processing techniques including, but not limited to, noise reduction, image resizing, color correction, segmentation, feature extraction, gray scaling, etc. The applied image pre-processing techniques may be selected to normalize and/or otherwise prepare each individual page image for processing by one or more trained models, as discussed in greater detail below.

In some embodiments, the anthology document 252 is received in a format including and/or interpretable as image input data 354 and the image processing module 352 is omitted and/or simplified. For example, in some embodiments, the anthology document 252 is received in a format, such as a PDF file, multiple TIFF files, etc., in which each page in the anthology document 252 is stored and/or interpretable as an individual image file. In such embodiments, the image processing module 352 may be configured to split the anthology document 252 into individual page images without applying any additional image processing and/or may be omitted.

In some embodiments, a document processing engine 254 includes a text processing module 356 configured to extract text input data 358 from the anthology document 252. The text input data 358 may include machine-readable text extracted from each page in the anthology document 252. The text processing module 356 may be configured apply a optical character recognition (OCR) process to generate text input data 358 including one or more text files. The text files may include any suitable format, such as, for example, a JavaScript Object Notation (JSON), an I-Object, a YAML file, etc.

In some embodiments, the text processing module 356 is configured to apply one or more pre-processing techniques to the anthology document 252 and/or the text input data 358. The text processing module 356 may be configured to apply processing techniques including, but not limited to, lower casing, tokenization, punctuation removal, stop word removal, stemming, lemmatization, etc. The applied text pre-processing techniques may be selected to normalize and/or otherwise prepare the text input data 358 for processing by one or more trained models, as discussed in greater detail below.

In some embodiments, the anthology document 252 is received in a format including interpretable text content and the text processing module 356 is omitted and/or simplified. For example, in some embodiments, the anthology document 252 is received in a format, such as a PDF file format, a Word file format, a text file format, etc., in which the text of the anthology document 252 is pre-recognized and/or otherwise machine interpretable within the format. In such embodiments, the text processing module 356 may be configured to extract the text of the anthology document 252 without applying any additional text processing and/or pre-processing and/or may be omitted.

At step 304, page class predictions (e.g., classifications) for each page in a anthology document 252 are generated. In some embodiments, the document processing engine 254 includes a multimodal extraction model 360 configured to receive at least two input datasets both representative of at least a portion of the anthology document 252, such as image input data 354 and text input dataset 358, and generate a page prediction 362 for each page in the anthology document 252. Although embodiments are discussed herein including two input datasets, it will be appreciated that the multimodal extraction model 360 may be configured to receive any suitable number of input datasets.

In some embodiments, the multimodal extraction model 360 includes a trained machine learning model comprising a plurality of integrated hidden layers configured to receive each of the input datasets 354, 358 and output a page prediction 362 for each page in the anthology document 252. The multimodal extraction model 360 may be configured to classify each page into one of a plurality of predetermined classifications, such as, for example, a "first page", a "middle page", a "last page", a "non-clinical page", etc. In some embodiments, a "first page" includes a page that signifies and/or identifies a start of an encounter record, a "middle page" includes a page that is neither the beginning nor end of an encounter record, a "last page" includes a page that completes and/or closes an encounter record, and a "non-clinical" page includes a page that is either not related to any encounters and/or that is excluded from use in coding for the corresponding domain. For example, with respect to medical records, certain information and/or encounters may be excluded from use in a code identification process by applicable rules, laws, and/or regulations.

In some embodiments, the multimodal extraction model 360 generates a page prediction 362 including classification of each page of a anthology document 252 into one of a set of predetermined categories. Table 1 illustrates an example a page prediction 362 from a multimodal extraction model 360 for a anthology document 252 having 7 pages:

TABLE 1

| Document Page Number | Original Label | Predicted Label |
|---|---|---|
| 1 | First-Page | First-Page |
| 2 | Middle-Page | Middle-Page |
| 3 | Last-Page | Last-Page |
| 4 | Non-Clinical | Non-Clinical |
| 5 | First-Page | Middle-Page |
| 6 | Middle-Page | Middle-Page |
| 7 | Last-Page | First-Page |

As shown in Table 1, the multimodal extraction model 360 identified a predicted "Middle Page" classification for page 5, which was originally classified as a first page in the anthology document 252, and a "First Page" for page 7, which was originally classified as a last page in the anthology document 252.

In some embodiments, the multimodal extraction model 360 is an ensemble model including two or more trained machine learning models, each configured to process a portion of the input datasets 354, 358. For example, the multimodal extraction model 360 may include an image processing model, a text processing model, and/or a combinatorial model. Each of the processing models may be configured to process at least a portion of each page of the anthology document 252 to identify elements for classification or identification of individual encounters within the anthology document 252. The processing models may be executed in series and/or in parallel, may be independent and/or at least partially dependent, and/or may include shared and/or redundant processes.

In some embodiments, the multimodal extraction model 360 is generated by a training process applying a domain-specific corpus. For example, a multimodal extraction model 360 may be generated by a training process applying a training dataset including domain-specific documents each having one or more encounters and a domain-specific corpus of terms associated with one or more of the encounter types within the domain. As one non-limiting example, a multimodal extraction model 360 trained to construct individual encounter records 256 from medical anthology documents may be trained on a domain-specific corpus of terms corresponding to medical encounters, (e.g., doctor visits, medical testing, procedures, notes). The domain-specific corpus may include and/or integrate terms used in one or more corresponding code libraries 253 and/or may be at least partially independent of the domain-specific code libraries 253.

In some embodiments, the multimodal extraction model 360 may include be configured to extract one or more additional types of structure data, such as, for example, from a data pipeline. The structured data may be identified during a training process and/or the multimodal extraction model 360 may be retrained or fine-tuned to extract additional or alternative types of structured data.

At step 306, a set of constructed individual encounter records 366 is generated based on the page prediction 362. In some embodiments, the page prediction 362 is provided to a post-processing module 364 configured to generate the set of constructed individual encounter records 366. The individual pages of the anthology document 252 may be combined based on the page prediction 362 for the corresponding page to generate constructed individual encounter records 366. Each of the constructed individual encounter records 366 includes one or more of the individual pages of the anthology document 252.

In some embodiments, the post-processing module 364 is configured to apply a rule set including one or more rules to construct individual encounters from the anthology document 252. For example, a rule set applied by the post-processing module 364 may indicate that a new individual encounter is started or delineated for each predicted "first page" in the anthology document 252 and that an individual encounter is closed for each predicted "last page" in the anthology document 252. As another example, in some embodiments, the post-processing module 364 may be configured to implement one or more rules such as a "first page" cannot follow a "middle page" in a constructed individual encounter to identify encounters lacking an expected structure (e.g., first page, middle page(s), last page). As still another example, in some embodiments, the post-processing module 364 may be configured to apply prediction thresholds to determine a confidence of one or more predictions and select page assignments and/or construct individual encounters based on one or more probabilities for individual page predictions. Although certain embodiments are discussed herein, it will be appreciated that any suitable post-processing logic configured to consider and/or manipulate the page predictions (either individually and/or in the aggregate) to construct encounters may be applied.

An example set of constructed individual encounter records 366 generated from the example page prediction 362 illustrated in Table 1 is illustrated in Table 2:

TABLE 2

| Encounter Number | Start Page | End Page |
|---|---|---|
| 1 | 1 | 3 |
| 2 | 5 | 6 |
| 3 | 7 | 7 |

As illustrated in Table 2, an anthology document 252 including 7 pages may be separated into a constructed individual encounter record 366 including three individual encounters, a first encounter including pages 1-3, a second encounter including pages 5-6, and a third encounter including page 7. It will be noted that page 4, which was identified as a "non-clinical" page is excluded from the constructed individual encounter record 366. The constructed individual encounter record 366 and/or the individual encounter records 256 may include data similar to that shown in Table 2, may include the pages of the anthology document 252 divided according to data similar to that shown in Table 2, and/or may include any other suitable delineation of the identified encounters in the anthology document 252.

In some embodiments, the multimodal extraction model 360 and/or the post . . . processing module 364 are configured to prevent cascading errors that may occur based on individual misidentification of encounter or page types within an anthology document 252. For example, although application of multiple individual trained models, each configured to identify an individual encounter type (e.g., office visits, lab results), may allow for identification of certain encounters within an anthology document 252, the use of multiple models creates a risk of cascading errors in which a first model incorrectly identifies a page as belonging to a first type of encounter when in fact it belongs to a second type of encounter, resulting in subsequent models incorrectly identifying other pages as being part of and/or excluded from subsequent target encounter types. The application of multiple models, and the hidden nature of the underlying layers, may make identification of the source of cascading errors impossible in a multiple model system. In some embodiments, the use of a multimodal extraction model 360 avoids such potential errors and prevents cascading misidentification of pages and/or encounters by providing a single model that receives input datasets 354, 358 and generates a page prediction 362 for all pages in a document and all types of encounters simultaneously. Similarly, the post-processing module 364 can apply one or more rules configured to prevent cascading misidentification of pages within the constructed individual encounter record.

At optional step 308, encounter metadata 370 is generated for each encounter in the constructed individual encounter record 366. Encounter metadata 370 may include any suitable metadata associated with and/or extractable from an encounter. For example, in some embodiments, encounter metadata 370 may include, but is not limited to, signature metadata (indicating whether a clinician and/or other individual signature is present), date of service metadata (indicating a date of service associated with the encounter or page of the encounter), provider name metadata (indicating a provider name for the encounter and/or page of the encounter), note type metadata (indicating a notation type of the encounter), etc.

Encounter metadata 370 may be determined on a page-wise and/or encounter-wise basis. For example, in some embodiments, encounter metadata 370 such as signature metadata, provider name metadata, data of service metadata, etc. may be determined for each page in a constructed encounter. As another example, in some embodiments, encounter metadata 370 such as note type metadata may be determined for each constructed encounter in a set of constructed individual encounter records 366. The extracted and/or determined encounter metadata 370 may be selected based on the requirements of a downstream resource data structure generation process, as described in greater detail below.

In some embodiments, encounter metadata 370, such as page-wise encounter metadata, may be generated and/or predicted prior to generating the constructed individual encounter records 366. For example, page-wise encounter metadata may be generated for the anthology document 252 as a first step of the encounter construction method 300, e.g., prior to division and/or processing of the anthology document 252 into constructed encounters in a constructed individual encounter record 366. Page-wise metadata may be generated for each page in the anthology document 252. In some embodiments, page-wise metadata is provided as an input to a multimodal extraction model 360 and/or a post-processing module 364 and used as part of a page prediction and/or encounter construction process.

In some embodiments, encounter metadata 370 can include encounter entity metadata, such as metadata identifying an entity type of data elements and/or textual elements identified within individual pages and/or constructed encounters. For example, encounter metadata 370 may include an entity type identification including, but not limited to, lab, medications, conditions, drugs, devices, symptoms, etc. Although specific embodiments are discussed herein, it will be appreciated that any suitable encounter metadata 370 may be extracted from individual pages and/or constructed encounters within the anthology document 252.

In some embodiments, the encounter metadata 370 is generated by a metadata module 368. The metadata module 368 is configured to receive the constructed individual encounter record 366 and identify metadata within each of the individual encounter records. The metadata module 368 may be configured to apply any suitable process, model, engine, module, etc. to delineate, extract, and/or otherwise identify encounter metadata 370 for one or more of the individual encounters in the constructed individual encounter record 366.

At step 310, the set of constructed individual encounter records 366, and any optionally generated encounter metadata 370, is output as a set of individual encounter records 256. The set of individual encounter records 256 may be output in any suitable format, such as, for example, a format expected by a value set generation engine 262, described in greater detail below. Although a single set of individual encounter records 256 is illustrated, it will be appreciated that the set of individual encounter records 256 may be output in any suitable format, such as, for example, multiple individual files each representative of a constructed encounter and associated metadata, a single file including delineations of constructed encounters, etc.

With reference again to FIGS. 3-4, at step 206, one or more resource data structures 260 are generated based each record in the set of individual encounter records 256. For example, in some embodiments, a resource generation engine 258 is configured to generate one or more resource data structures 260. The resource generation engine 258 may be configured to apply one or more trained models, such as one or more trained natural language processing models, and/or one or more rules-based models to extract textual and/or contextual data from each of the records in the set of individual encounter records 256 and generate resource data structures 260 representative of potentially codeable elements and/or supporting information extracted from the set of individual encounter records 256.

Figure 7:
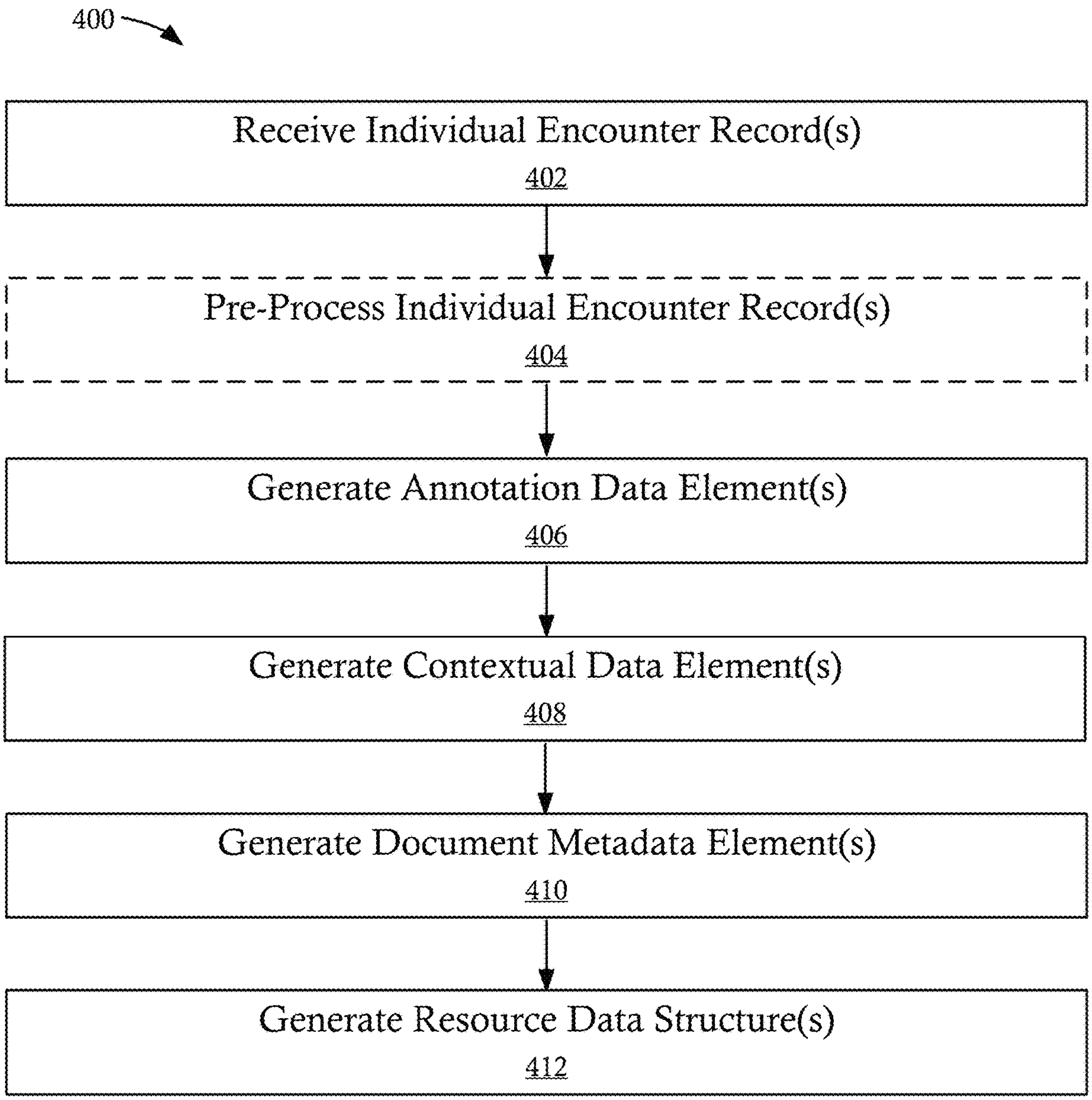
FIG. 7 is a flowchart illustrating a resource data structure generation method, in accordance with some embodiments.
Figure 8:
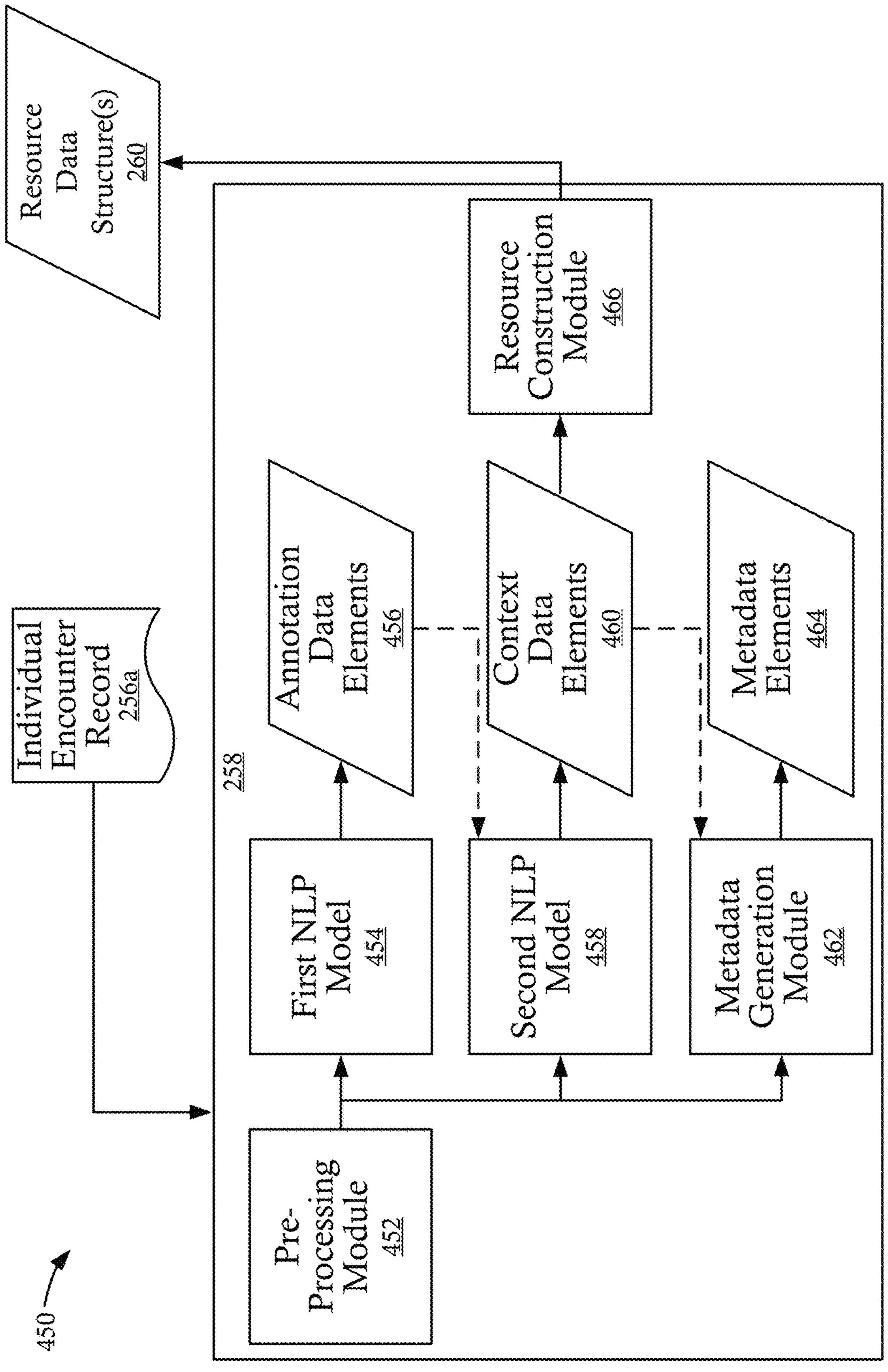
FIG. 8 is a process flow illustrating various steps of the resource data structure generation method of FIG. 7, in accordance with some embodiments.

FIG. 7 is a flowchart illustrating a resource data structure generation method 400, in accordance with some embodiments. FIG. 8 is a process flow 450 illustrating various steps of the resource data structure generation method 400, in accordance with some embodiments. At step 402, an individual encounter record **256*a* is received. The individual encounter record 256*a* may include a constructed encounter extracted from and/or delineated in an anthology document 252. For example the individual encounter record 256*a* may be identified according to the encounter construction method 300 discussed above. In some embodiments, the individual encounter record 256*a* is received by the value set generation engine 262**.

At optional step 404, the individual encounter record **256*a* is pre-processed. For example, in some embodiments, a pre-processing module 452 may be configured to apply one or more pre-processing techniques configured to generate pre-process data elements, such as, for example, an OCR process configured to generate OCR data, text processing, etc. In some embodiments, the individual encounter record 256*a* includes machine-readable text data and/or pre-processed text data (for example, text data processed as discussed above with respect to step 302 of the encounter construction method 300) and optional step 404** is omitted.

At step 406, one or more annotation data elements 456 are generated. The annotation data elements 456 may be generated by an entity identification process applied to identify or extract named entities from the individual encounter record **256*a* and/or classify extracted entities into one or more predefined classes. For example, in some embodiments, a first trained natural language processing (NLP) model 454 is configured to implement an NLP-based named entity recognition subprocess to identify n-grams (e.g. one or more words or phrases) in the individual encounter record 256*a* corresponding to known named entities defined in one or more entity dictionaries. In some embodiments, the one or more entity dictionaries are domain-specific and correspond to the same and/or a similar domain as that of the code library 253**. For example, in some embodiments, the one or more entity dictionaries include entities associated with a medical coding library, such as, for example, conditions, diseases, diagnosis, etc. that have one or more associated codes in a corresponding medical coding library.

Figure 9:
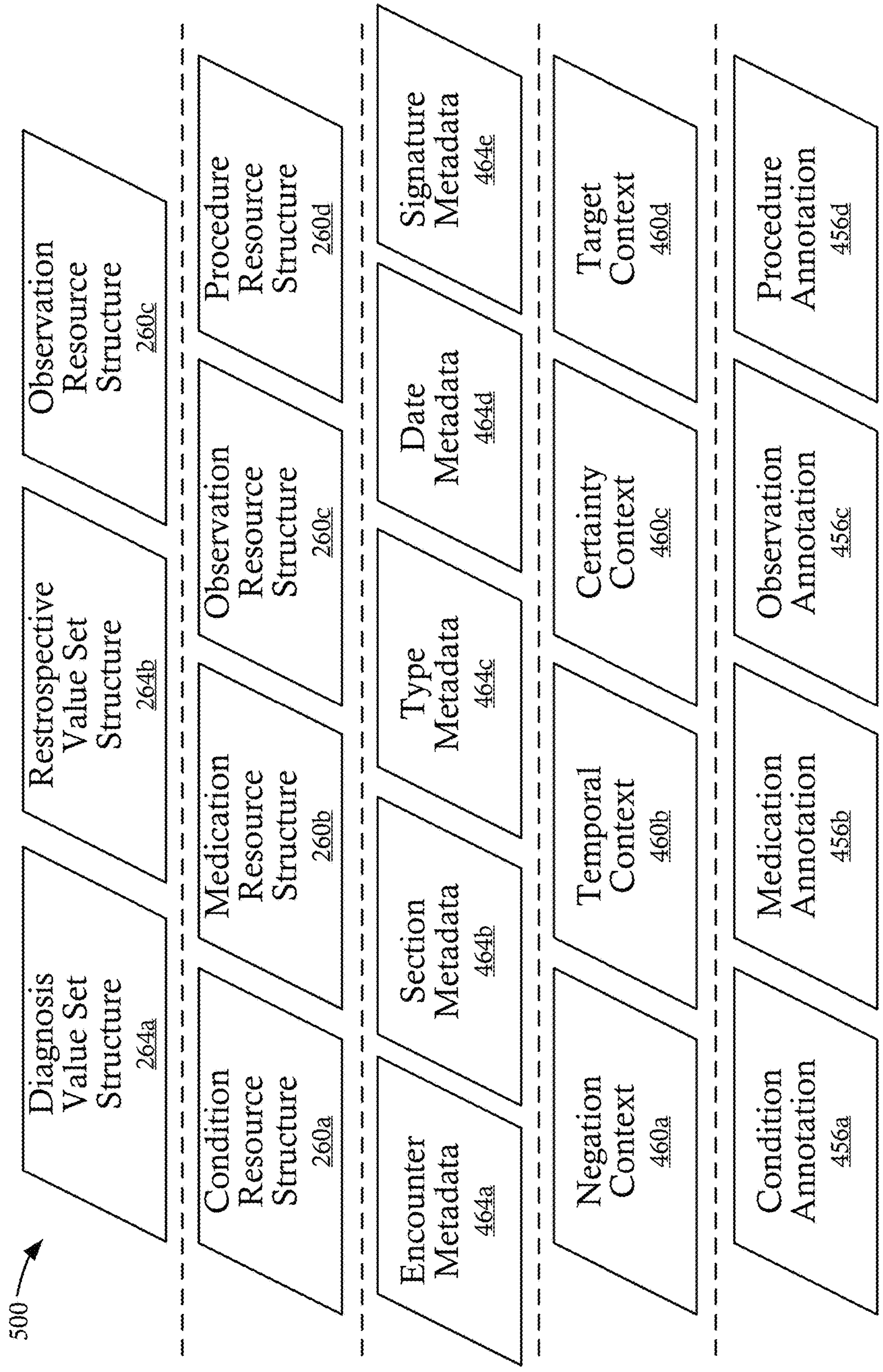
FIG. 9 illustrates a hierarchical stack of various data processing elements generated in conjunction with the code extraction and review method of FIG. 3 and/or sub processes, such as the resource data structure generation method of FIG. 7, in accordance with some embodiments.
Figure 10:
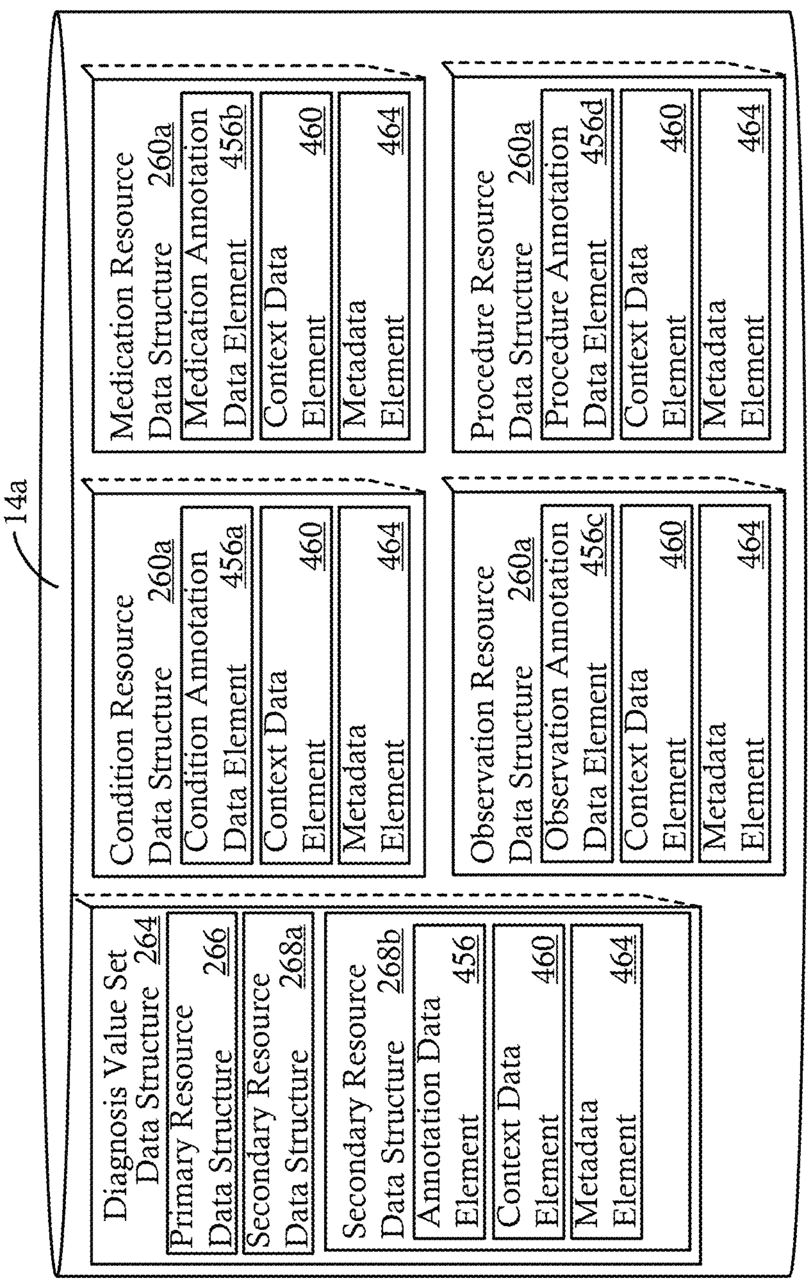
FIG. 10 illustrates a database including hierarchical data structures generated as part of and/or in response to the code extraction and review method of FIG. 3 and/or sub processes, such as the resource data structure generation method of FIG. 7, in accordance with some embodiments.

FIG. 9 illustrates a hierarchical stack 500 of various data processing elements generated in conjunction with the code extraction and review method 200 and/or sub processes, such as the resource data structure generation method 400, in accordance with some embodiments. FIG. 10 illustrates a database **14*a* including hierarchical data structures generated as part of and/or in response to the code extraction and review method 200 and/or sub processes, such as the resource data structure generation method 400, in accordance with some embodiments. In the example embodiment illustrated in FIGS. 9 and 10, annotation data elements 456 may include, but are not limited to, condition annotation data elements 456*a*, medication annotation data elements 456*b*, observation annotation data elements 456*c*, procedure annotation data elements 456*d***, etc.

With reference again to FIGS. 7-8, in some embodiments, a trained natural language processing model, such as the first trained NLP model 454 and/or an additional trained natural language processing model, is configured to further classify each extracted entity into one of a plurality of predetermined categories. For example, in embodiments corresponding to a medical domain, each extracted entity may be classified into one of a plurality of categories including, but not limited to, condition annotations, medication annotations, observation annotations, procedure annotations, etc. The predetermined categories may be defined by one or more domain configurations applied during the training process of the first trained NLP model 454 and/or defined by the one or more entity dictionaries that correspond to a domain of the processed individual encounter record **256*a* and/or the code library 253. In some embodiments, each of the annotation data elements 456** include an extracted entity and a corresponding classification.

At step 408, one or more context data elements 460 are generated for one or more of the annotation data elements 456. Context data elements 460 may include, but are not limited to, negation context data elements **460*a*, temporal context data elements 460*b*, certainty context data elements 460*c*, target context data elements 460*d*, etc. (see FIG. 10) Negation context data elements 460*a* are representative of the presence (e.g., positive assertion) or absence (e.g., negative assertion) of an associated annotation data element 456*a*-456*d*. For example, a statement that a patient "was not exhibiting signs of heart attack" or that a patient "does not have elevated blood pressure" indicates that the associated entity, e.g., heart attack or elevated blood pressure, was not observed/present. Alternatively, a statement that a patient "presented with" or "was admitted due to" heart attack or elevated blood pressure indicates that the associated entity was observed/present. Temporal context data elements 460*b* may indicate a time period for an associated entity. For example, an indication that a patient "was seen two years ago for heart attack" indicates a past occurrence of the associated entity (e.g., heart attack) while an indication that a patient was "admitted today for heart attack" indicates an occurrence of the associated entity contemporaneously with creation of the individual encounter record 256*a*. Certainty context data elements 460*c* may provide a confidence or probability for an associated entity. For example, a differential diagnosis of an associated entity may have a lower probability or certainty as compared to an express diagnosis of the same entity. Target context data elements 460*d*** may be used to identify the person or target who experienced or is associated with the identified named entity. For example, an indication that a patient is experiencing/has experienced a condition indicates the experiencer is the patient, while an indication that a family member has experienced a condition indicates that experiencer is not the patient.

In some embodiments, the context data elements 460 are generated by a second trained natural language model 458 configured to apply an NLP-based contextual generation process. The second trained natural language model 458 may be configured to identify n-grams located in proximity to and/or referencing an annotated named entity, e.g., one of the annotation data elements 456, and extract (e.g., generate) context (e.g., themes, facets, parts of speech, sentence structure) based on the associated n-grams. Although embodiments are illustrated including a first trained NLP model 454 and a second trained NLP model 458, it will be appreciated that the first and second trained NLP models 454, 458 may be combined into a single NLP model. The single NLP model may include integrated layers and/or distinct layers configured to generate the annotation data elements 456 and generate the context data elements 460.

At step 410, document metadata elements 464 may be generated and/or obtained for the individual encounter record **256*a*. Metadata elements 464 may include, but is not limited to, encounter metadata 464*a*, section metadata 464*b*, type metadata 464*c*, date metadata 464*d*, signature metadata 464*e*, etc. The metadata elements 464 may include encounter metadata 370 generated by the encounter construction method 300, as discussed in greater detail above, and/or metadata generated by a separate metadata generation module 462. In some embodiments, metadata elements 464 may be generated for the individual encounter record 256*a* and/or a portion of the individual encounter record 256*a* corresponding to one or more of the annotation data elements 456**.

In some embodiments, the metadata generation module 462 includes a rules-based analysis engine configured to apply a set of rules for generating and/or extracting document metadata. For example, in some embodiments, the metadata generation module 462 may apply one or more rules configured to exclude certain portions of the individual encounter record **256*a*, generate metadata based on the structure of the individual encounter record 256*a*, and/or otherwise generate appropriate metadata for the individual encounter record 256*a*. Although embodiments are discussed herein including a rules-based metadata generation module 462, it will be appreciated that the metadata generation module 462 may alternatively and/or additionally include any suitable process, such as, for example, a machine learning-based process as discussed above with respect to the encounter construction method 300**.

At step 412, one or more resource data structures 260 are constructed. Each of the resource data structures 260 includes one of the annotation data elements 456 that supports and/or recommends selection of one or more codes from the code library 253. In some embodiments, each of the resource data structures 260 includes an annotation data element 456 and may include a category classification corresponding to the category of the associated one of the annotation data elements 456. To continue the example from above, in embodiments including classification of annotation data elements 456 as one of a condition annotation data element **456*a*, a medication annotation data element 456*b*, an observation annotation data element 456*c*, or a procedure annotation data element 456*d*, each of the resource data structures 260 may be classified as a condition resource data structure 260*a*, a medication resource data structure 260*b*, an observation resource data structure 260*c*, or a procedure resource data structure 260*d* (see FIG. 10), based on the classification of the annotation data element 456*a*-456*d* associated with the resource data structure 260*a*-260*d*. Each of the resource data structures 260 may further include an aggregation of previously generated data, such as an associated one of the annotation data elements 456, the context data elements 460 corresponding to the identified one of the annotation data elements 456 entity, the metadata elements 464 corresponding to the identified one of the annotation data elements 456**, and/or any other corresponding data.

In some embodiments, each of the resource data structures 260 is generated by a resource construction module 466. The resource construction module 466 may include a rules-based engine configured to apply a set of rules to previously generated data, such as one of the annotation data elements 456, a context data element 460 associated with the selected one of the annotation data elements 456, metadata elements 464 associated with the selected one of the annotation data elements 456, etc., to determine when a resource data structure 260 is to be generated. For example, a first rule may dictate that a resource data structure 260 is not generated for a negative annotation data element, i.e., if negation context data element **460*a* associated with a selected annotation data element indicates a negative context (e.g., "the patient did not have elevated blood pressure), the corresponding entity (e.g., elevated blood pressure) was not present and the annotation data element 456 corresponding to the "elevated blood pressure" entity can be ignored. As another example, a second rule may dictate that a resource data structure 260 is not generated for preexisting conditions as determined by temporal context data elements 460*b*, e.g., if the temporal context data element 460*b* associated with a selected annotation data element indicates a time period outside of a specific threshold (e.g., greater than 1 month, 2 months, 1 year), the annotation data element 456 corresponding to that entity may be discarded. As yet another example, a third rule may dictate that a resource data structure 260 is not generated for an annotation data element 456 directed to persons other than a current patient. For example, if target context data elements 460*d* indicates a target of a person other than the patient associated with the individual encounter record 256*a* (such as a family member), a resource data structure 260 is not generated for the corresponding annotation data element 456. As still another example, a fourth rule may dictate that a resource data structure 260** is not generated when the metadata element 464 associated with an annotation data element 456 indicates the entity associated with the annotation data element 456 was found in a "history" note section. Although specific examples are discussed herein, it will be appreciated that any suitable rule set including any suitable rules may be applied to generate one or more resource data structures 260.

The resource generation module 466 may be configured to apply a set of rules sequentially (e.g., in series) and/or simultaneously (e.g., in parallel). The resource generation module 466 may be configured to apply any suitable set of rules defining any suitable conditions based on the previously generated data. For example, a rules-based resource generation module 466 may apply a set of rules that results in generation of a resource data structure 260 when an annotation data element 456 is associated with (e.g., includes) a positive negation context (e.g., indicating the identified entity is present), an immediate or short term temporality context, a high certainty context, a patient experiencer, and metadata indicating the encounter was an office visit and was signed by a practitioner. Although specific embodiments are discussed herein, it will be appreciated that any suitable rules and/or heuristics based on any of the annotation data elements 456, context data elements 460 corresponding to one of the annotation data elements 456, metadata elements 464 corresponding to one of the annotation data elements 456, etc. may be utilized to determine when to generate a resource data structure 260 and/or data to be included in the resource data structure 260.

In some embodiments, each of the resource data structures 260 includes an aggregation of one or more data elements. For example, a resource data structure 260 may include a selected annotation data elements 456, one or more context data elements 460 associated with selected annotation data elements 456, one or more metadata elements 464 associated with selected one of the annotation data elements 456, etc. In some embodiments, each of the resource data structures 260 includes a category data element. The category data element may include a category corresponding to a category of the selected annotation data element 456. For example, a condition resource data structure 260*a* includes a condition annotation data element 456*a*, a medication resource data structure 260*b* includes a medication annotation data element 456*b*, an observation resource data structure 260*c* includes an observation annotation data element 456*c*, a procedure resource data structure 260*d* includes a procedure annotation data element 456*d*, etc.

With reference again to FIGS. 3-4. at step 208, one or more value set data structures 264 are generated. Each of the value set data structures 264 is representative of a codeable element extracted from an individual encounter record 256. A codeable element includes a domain-specific element having a corresponding code in the domain-specific code library 253. For example, in the context of a medical domain and a clinical condition code library (e.g., ICD-10), a codeable element may include a condition (e.g., disease, disorder, etc.), procedure, diagnosis, etc. that has a corresponding code in the domain-specific code library 253. Although specific embodiments are discussed herein, it will be appreciated that a codeable element may include any suitable domain-specific element that includes a corresponding code in a domain-specific code library 253.

In some embodiments, each of the value set data structures 264 includes a primary resource data structure 266 selected from the resource data structures 260, an optional set of supporting data structures 268*a*-268*b* selected from the resource data structures 260, and a code data element 270 corresponding to a code selected from the domain-specific code library 253. Each of the value set data structures 264 may further include a type or category designation based on, for example, a category associated with the primary resource data structure 266. For example, in the context of an anthology document 252 including a medical record and associated medical domain-specific code library 253, a value set data structure 264 may include one or more of a diagnosis value set data structure 264*a*, a retrospective clinical indicator value set data structure 264*b*, a building block value set data structure 264*c*, etc. (see FIG. 10). In some embodiments, a diagnosis value set data structure 264*a* may include primary resource data structure 266 including a condition annotation data element 456*a* and a code data element 270 representative of a codified condition corresponding to the condition annotation data element 456*a*, a retrospective clinical indicator value set data structure 264*b* may include a primary resource data structure 266 including a procedure annotation data element 456*d* and a code data element 270 representative of a codified condition that is treated by and/or associated with the procedure of the procedure annotation data element 456*d*, a building block value set data structure 264*c* may include a primary resource data structure 266 representative of semantically-related concepts that represent a distinct idea within a setting or lexicon (e.g., a clinical setting).

As one non-limiting example, within the context of a clinical setting, primary resource data structure 266 may include, but is not limited to, data representative of concepts such as "diabetes," "hand joint pain," "weight reduction diet," "MRI cervical spine, "Prostate-specific antigen (PSA) abnormality," etc. The primary resource data structures may be extracted from value sets that are non-specific to one or more domains (e.g., a risk adjustment domain) and curated within one or more contexts or other domains (e.g., a clinical context). Non-limiting examples include ICD-10, SNOMED, RxNorm, LOINC, CPT, etc.

In some embodiments, each value set data structure 264 is generated by a value set generation engine 262. The value set generation engine 262 may include a rules-based engine configured to apply a set of high-touch rules configured to identify one or more of a primary resource data structure 266, supporting resource data structures 268*a*, 268*b*, and/or a code data element 270. For example, in some embodiments, the value set generation engine 262 includes a first rule set configured to identify a primary resource data structure 266. As one example, the first rule set may include one or more rules configured to select a primary resource data structure 266 from the resource data structures 260 of a specific category, such as condition resource data structures 260*a*. As another example, the first rule set may include one or more rules configured to select a primary resource data structure 266 from the resource data structures 260 of a secondary category if no resource data structures 260 of a first category are available, e.g., selecting procedure resource data structures 260*d* if there are no condition resource data structures 260*a* available for selection.

In some embodiments, the value set generation engine 262 includes a second rule set configured to identify supporting resource data structures 268*a*, 268*b*. As one example, the second rule set may include one or more rules configured to select secondary resource data structures 268*a*, 268*b* from the resource data structures 260 of one or more specific categories, such as medication resource data structures 260*b* and/or observation resource data structures 260*c*. As another example, the second rule set may include one or more rules configured to select secondary resource data structures 268*a*, 268*b* from the resource data structures 260 having similar context data elements 460 and/or metadata elements 464 as the primary resource data structure 266.

In some embodiments, the value set generation engine 262 includes a third rule set configured to identify a code data element 270 including a code selected from the code library 253. As one example, the third rule set may be configured to identify a code within the code library 253 based on the primary resource data structure 266 and/or the secondary resource data structures 268*a*, 268*b*. Although specific embodiments are discussed herein, it will be appreciated that any suitable rules set may be applied to select and/or generate any portion of the value set data structures 264.

In some embodiments, the value set generation engine 262 may include a trained model configured to identify one or more data elements, such as a code data element 270. For example, the value set generation engine 262 may include a trained NLP model configured to select a code from the code library 253 based on a correspondence between portions of the anthology document 252, as represented by each of the resource data structures 266, 268*a*, 268*b* corresponding to a specific value set data structure 264. The NLP model may be configured to apply a similarity determination, such as a vector similarity (e.g., a cosine similarity) determination, to identify a code in the code library 253 having a textual description closest to the elements represented in the resource data structures 266, 268*a*, 268*b*. Although specific embodiments are discussed herein, it will be appreciated that any suitable trained model and/or rules-based process may be used to identify a code data element 270 for each of the value set data structures 264.

In some embodiments, the value set generation engine 262 is configured to apply a scoring subprocess to generate a confidence score for a value set data structure 264. The scoring subprocess may generate individual confidence point values for each of the primary resource data structure 266 and/or the secondary resource data structures 268*a*, 268*b*. The individual confidence point values may be determined according to any suitable process, such as a rules-based process, a machine learning-based process, etc. A confidence score is determined for a value set data structure 264 by aggregating (e.g., summing) the individual confidence point values associated with each of the primary resource data structure 266 and/or the secondary resource data structures 268*a*, 268*b*. In some embodiments, a value set data structure 264 is only generated when the aggregate score is equal to or greater than a predetermined threshold and is not generated when the aggregate score is less than a predetermined threshold. In some embodiments, a value set data structure 264 may include a data element indicating a confidence level of the value set data structure 264 based on the aggregate score, for example, assigning a confidence level corresponding to a range of aggregate scores to each generated value set data structure 264.

In some embodiments, a rules-based process is configured to assign each of the primary resource data structure 266 and/or the secondary resource data structures 268*a*, 268*b* to one of a plurality of categories corresponding to a confidence level for a selected code data element 270 based on the respective resource data structure 266, 268*a*, 268*b*. For example, each resource data structure 266, 268*a*, 268*b* may be classified in one of three categories: a high confidence category, a moderate confidence category, or a low confidence category. The rules-based process may include rules associating each category and/or each individual resource data structure 260 to one of the plurality of categories.

In some embodiments, each of the categories (e.g., high confidence, moderate confidence, low confidence) has a confidence point value associated therewith. For example, a high confidence level may have a value of X points associated therewith, a moderate confidence level may have a value of Y points associated therewith, and a low confidence level may have a value of Z points associated therewith, where X>Y>Z. An aggregated confidence score (CS) for a value set data structure 264 may be generated by summing the confidence point value assigned to each resource data structure 260 in the subset of resource data structures 266, 268*a*, 268*b* associated with the value set data structure 264, e.g.:

$$CS = \sum_{1}^{i} f_{CP}(X_i)$$

where $f_{CP}$ is a functional representation of the rules structure configured to select a confidence point value for each resource data structure in the subset of resource data structures 266, 268*a*, 268*b*, *i* is the number of resource data structures in the subset of resource data structures 266, 268*a*, 268*b*, and $x_i$ is the $i^{th}$ data structure in the subset of resource data structures 266, 268*a*, 268*b*.

Although embodiments are discussed herein including separate steps and/or processes, it will be appreciated that two or more steps of each of the disclosed methods (e.g., the code extraction and review method 200, the encounter construction method 300, the resource data structure generation method 400) may be combined into a single step and/or performed during an integrated process. For example, in some embodiments, a trained natural language processing model includes multiple sets of trained layers. Each set of layers may be configured to perform one or more of the steps of the code extraction and review method 200. For example, a first set of layers may be configured to perform entity extraction and classification, a second set of layers may be configured to perform contextual awareness filtering, a third set of layers may be configured to perform document structure metadata analysis, and a fourth set of layers may be configured to generate resource data structures for use by subsequent layers, models, and/or processes. Although specific embodiments are discussed herein, it will be appreciated that any suitable combination of models and/or layers may be configured to perform one or more steps of the disclosed methods.

With reference again to FIGS. 3-4, at step 210, an annotated anthology document 252*a* is generated based on the one or more value set data structures 264. The annotated anthology document 252*a* includes the original anthology document 252 and linkage elements representing and/or identifying linkages between each resource data structure 266, 268*a*, 268*b* in a value set data structure 264 and the corresponding entities within the anthology document 252. The annotated anthology document 252*a* may be generated and stored in a database, such as database 14*a*, and/or may be generated in real time as part of an interface. In some embodiments, the linkages represented by the resource data structures 266, 268*a*, 268*b* are represented by visual elements embedded within the annotated anthology document 252*a*. For example, the annotated anthology document 252*a* may include highlighting or other color coding corresponding to each of the resource data structures 266, 268. In some embodiments, specific color coding may be used to indicate different resource data structures 266, 268, such as a first color denoting an entity associated with primary resource data structure 266 and a second color denoting an entity associated with each of the secondary resource data structures 268. Although specific embodiments are discussed herein, it will be appreciated that any suitable annotation scheme may be applied to illustrate or demonstrate linkages between entities within the annotated anthology document 252*a* and the resource data structures 266, 268.

In some embodiments, a code linkage engine 280 is configured to generate linkage data and/or linkage elements (e.g., visual elements) for each value set data structure 264 associated with an annotated anthology document 252*a*. The code linkage engine 280 identifies entities within the annotated anthology document 252*a* corresponding to the individual resource data structures 266, 268*a*, 268*b*. In some embodiments, the code linkage engine 280 is configured to allow traversal of linkages and/or data elements within the annotated anthology document 252*a*. For example, the code linkage engine 280 may facilitate linkage traversal from an entity in the annotated anthology document 252*a* to a corresponding value set data structure 264 and further allow traversal through the value set data structure 264 to each of the underlying elements, such as the resource data structures 266, 268*a*, 268*b*, the elements of the resource data structures 266, 268*a*, 268*b* (e.g., annotation data elements 456, context data elements 460, metadata elements 464). Similarly, the code linkage engine 280 may facilitate linkage traversal in an opposite direction, moving from an underlying element of a resource data structure 266, 268*a*, 268*b*, to the corresponding value set data structure 264 and/or the corresponding entity in the annotated anthology document 252*a*.

In some embodiments, a code interface 282 is generated. The code interface 282 is configured to display the annotated anthology document 252*a*, visual linkage elements 284*a*, 284*b* representative of the linkage data for one or more value set data structures 264, and the elements of the one or more corresponding value set data structures 264. The code interface 282 may be configured to provide programmatic linkage traversal of linkage data generated by the code linkage engine 280 and/or a separate interface generation module (not shown). The code interface 282 may be further configured to receive feedback regarding a selected code data element 270 for each of the associated value set data structures 264. In some embodiments, the code interface 282 is configured to display elements corresponding to the primary resource data structure 266 and each of the secondary resource data structures 268*a*, 268*b* of a selected value set data structure 264.

At step 212, feedback data 290 is received. In some embodiments, the feedback data 290 includes one of a confirmation or a rejection of a selected code data element 270 for one or more value set data structures 264. The feedback data 290 may be received using any suitable mechanism. For example, in some embodiments, the feedback data 290 is received via the code interface 282. As another example, in some embodiments, the feedback data 290 includes third party acceptance/rejection information regarding selected code data elements 270 (e.g., codes represented by the code data elements 270).

At step 214, one or more updated models 294 may be generated for use in subsequent execution of one or more engines, such as the document processing engine 254, the resource generation engine 258, etc. The updated models 294 may include one or more updated machine learning models, such as one or more updated NLP models, trained and/or refined based, at least in part, on the feedback data 290. For example, an updated training dataset may be generated by combining, augmenting, and/or modifying a prior training dataset based on the feedback data 290 to include additional labeled data representative of approved and/or rejected code identification for one or more annotated anthology documents 252*a* as determined by the feedback data 290.

Figure 11:
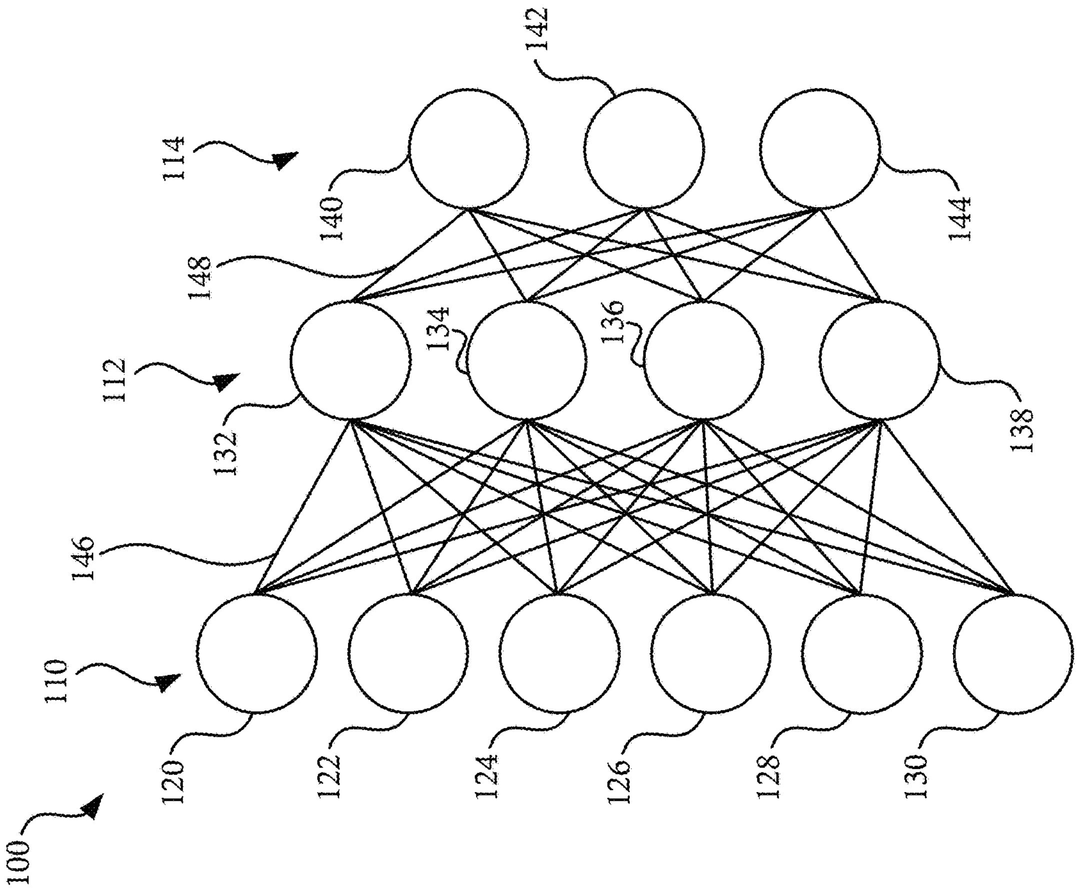
FIG. 11 illustrates an artificial neural network, in accordance with some embodiments.

FIG. 11 illustrates an artificial neural network 100, in accordance with some embodiments. Alternative terms for "artificial neural network" are "neural network," "artificial neural net," "neural net," or "trained function." The neural network 100 comprises nodes 120-144 and edges 146-148, wherein each edge 146-148 is a directed connection from a first node 120-138 to a second node 132-144. In general, the first node 120-138 and the second node 132-144 are different nodes, although it is also possible that the first node 120-138 and the second node 132-144 are identical. For example, in FIG. 3 the edge 146 is a directed connection from the node 120 to the node 132, and the edge 148 is a directed connection from the node 132 to the node 140. An edge 146-148 from a first node 120-138 to a second node 132-144 is also denoted as "ingoing edge" for the second node 132-144 and as "outgoing edge" for the first node 120-138.

The nodes 120-144 of the neural network 100 may be arranged in layers 110-114, wherein the layers may comprise an intrinsic order introduced by the edges 146-148 between the nodes 120-144 such that edges 146-148 exist only between neighboring layers of nodes. In the illustrated embodiment, there is an input layer 110 comprising only nodes 120-130 without an incoming edge, an output layer 114 comprising only nodes 140-144 without outgoing edges, and a hidden layer 112 in-between the input layer 110 and the output layer 114. In general, the number of hidden layer 112 may be chosen arbitrarily and/or through training. The number of nodes 120-130 within the input layer 110 usually relates to the number of input values of the neural network, and the number of nodes 140-144 within the output layer 114 usually relates to the number of output values of the neural network.

In particular, a (real) number may be assigned as a value to every node 120-144 of the neural network 100. Here, $$x_i^{(n)}$$

denotes the value of the i-th node 120-144 of the n-th layer 110-114. The values of the nodes 120-130 of the input layer 110 are equivalent to the input values of the neural network 100, the values of the nodes 140-144 of the output layer 114 are equivalent to the output value of the neural network 100. Furthermore, each edge 146-148 may comprise a weight being a real number, in particular, the weight is a real number within the interval [−1, 1], within the interval [0, 1], and/or within any other suitable interval. Here, $$w_{i,j}^{(m,n)}$$

denotes the weight of the edge between the i-th node 120-138 of the m-th layer 110, 112 and the j-th node 132-144 of the n-th layer 112, 114. Furthermore, the abbreviation $$w_{i,j}^{(n)}$$

is defined for the weight $$w_{i,j}^{(n,n+1)}.$$

In particular, to calculate the output values of the neural network 100, the input values are propagated through the neural network. In particular, the values of the nodes 132-144 of the (n+1)-th layer 112, 114 may be calculated based on the values of the nodes 120-138 of the n-th layer 110, 112 by $$x_j^{(n+1)} = f\left(\sum_i x_i^{(n)} \cdot w_{i,j}^{(n)}\right)$$

Herein, the function f is a transfer function (another term is "activation function"). Known transfer functions are step functions, sigmoid function (e.g., the logistic function, the generalized logistic function, the hyperbolic tangent, the Arctangent function, the error function, the smooth step function) or rectifier functions. The transfer function is mainly used for normalization purposes.

In particular, the values are propagated layer-wise through the neural network, wherein values of the input layer 110 are given by the input of the neural network 100, wherein values of the hidden layer(s) 112 may be calculated based on the values of the input layer 110 of the neural network and/or based on the values of a prior hidden layer, etc.

In order to set the values $$w_{i,j}^{(m,n)}$$

for the edges, the neural network 100 has to be trained using training data. In particular, training data comprises training input data and training output data. For a training step, the neural network 100 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 100 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $$\delta_j^{(n)}$$

may be recursively calculated as $$\delta_j^{(n)} = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on $$\delta_j^{(n+1)},$$

if the (n+1)-th layer is not the output layer, and $$\delta_j^{(n)} = \left(x_k^{(n+1)} - t_j^{(n+1)}\right) \cdot f'\left(\sum_i x_i^{(n)} \cdot w_{i,j}^{(n)}\right)$$

if the (n+1)-th layer is the output layer 114, wherein f is the first derivative of the activation function, and $$y_j^{(n+1)}$$

is the comparison training value for the j-th node of the output layer 114.

Figure 12:
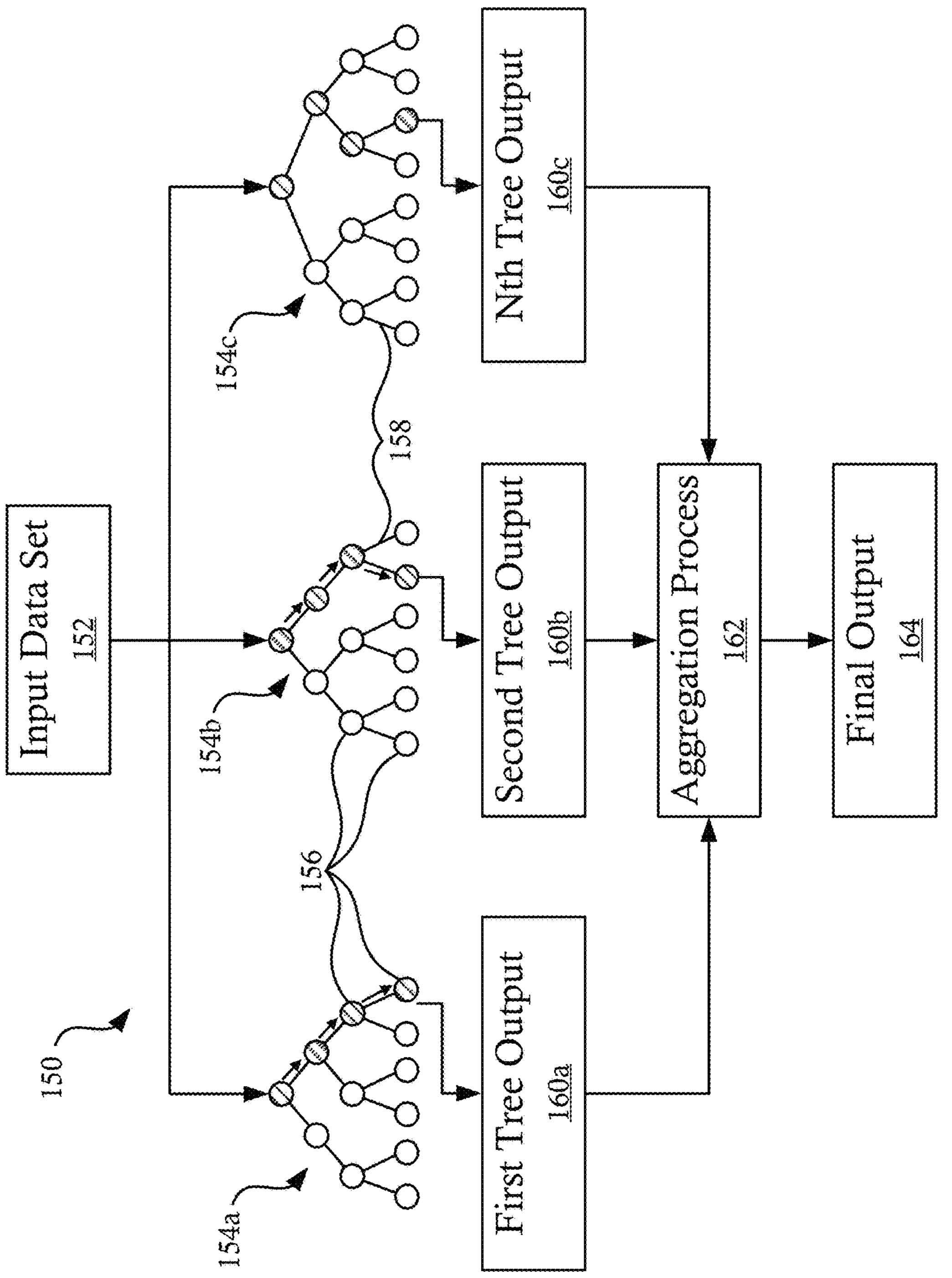
FIG. 12 illustrates a tree-based artificial neural network, in accordance with some embodiments.

FIG. 12 illustrates a tree-based neural network 150, in accordance with some embodiments. In particular, the tree-based neural network 150 is a random forest neural network, though it will be appreciated that the discussion herein is applicable to other decision tree neural networks. The tree-based neural network 150 includes a plurality of trained decision trees 154*a*-154*c* each including a set of nodes 156 (also referred to as "leaves") and a set of edges 158 (also referred to as "branches").

Each of the trained decision trees 154*a*-154*c* may include a classification and/or a regression tree (CART). Classification trees include a tree model in which a target variable may take a discrete set of values, e.g., may be classified as one of a set of values. In classification trees, each leaf 156 represents class labels and each of the branches 158 represents conjunctions of features that connect the class labels. Regression trees include a tree model in which the target variable may take continuous values (e.g., a real number value).

In operation, an input data set 152 including one or more features or attributes is received. A subset of the input data set 152 is provided to each of the trained decision trees 154*a*-154*c*. The subset may include a portion of and/or all of the features or attributes included in the input data set 152. Each of the trained decision trees 154*a*-154*c* is trained to receive the subset of the input data set 152 and generate a tree output value 160*a*-160*c*, such as a classification or regression output. The individual tree output value 160*a*-160*c* is determined by traversing the trained decision trees 154*a*-154*c* to arrive at a final leaf (or node) 156.

In some embodiments, the tree-based neural network 150 applies an aggregation process 162 to combine the output of each of the trained decision trees 154*a*-154*c* into a final output 164. For example, in embodiments including classification trees, the tree-based neural network 150 may apply a majority-voting process to identify a classification selected by the majority of the trained decision trees 154*a*-154*c*. As another example, in embodiments including regression trees, the tree-based neural network 150 may apply an average, mean, and/or other mathematical process to generate a composite output of the trained decision trees. The final output 164 is provided as an output of the tree-based neural network 150.

Figure 13:
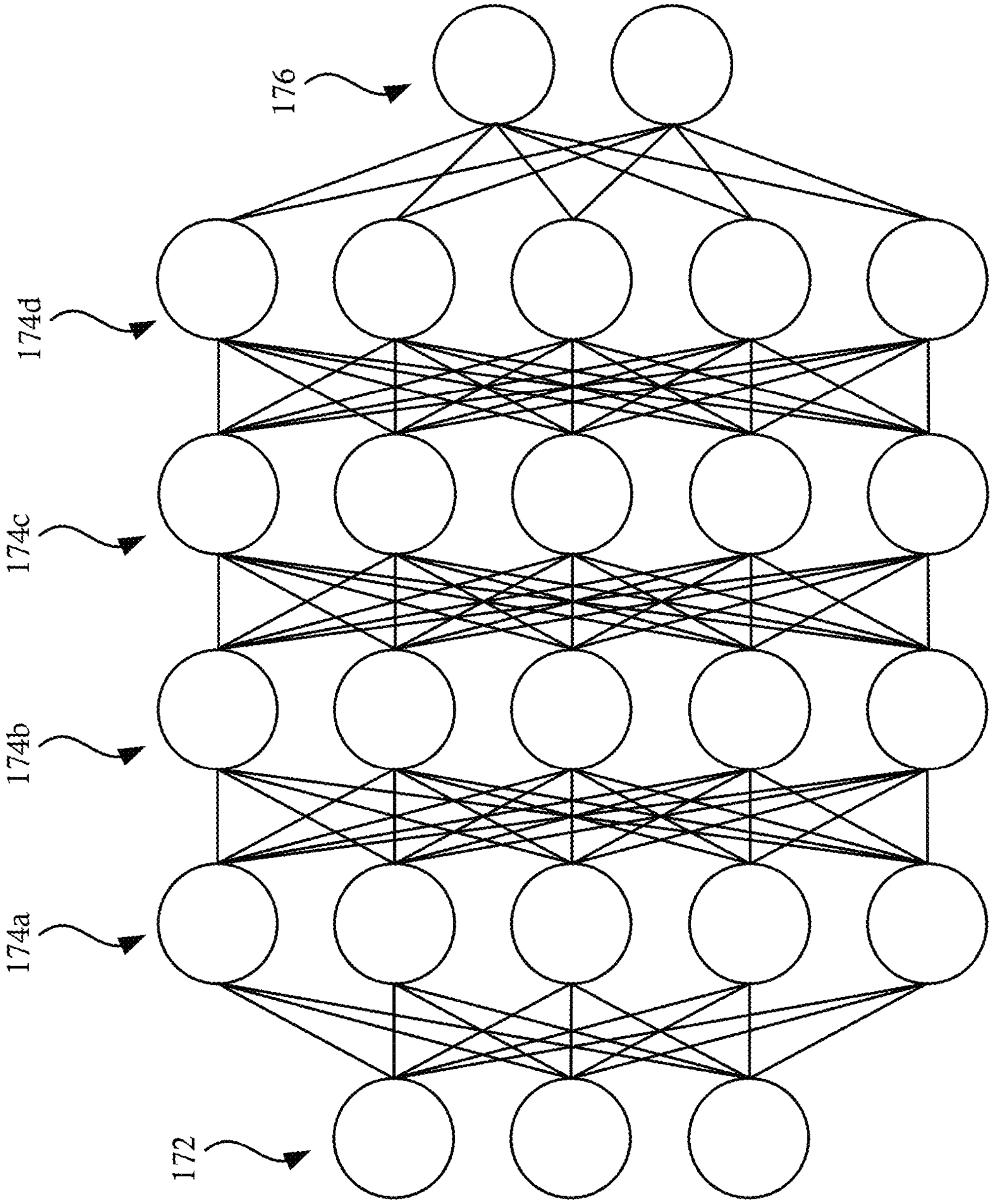
FIG. 13 illustrates a deep neural network (DNN), in accordance with some embodiments.

FIG. 13 illustrates a deep neural network (DNN) 170, in accordance with some embodiments. The DNN 170 is an artificial neural network, such as the neural network 100 illustrated in conjunction with FIG. 3, that includes representation learning. The DNN 170 may include an unbounded number of (e.g., two or more) intermediate layers 174*a*-174*d* each of a bounded size (e.g., having a predetermined number of nodes), providing for practical application and optimized implementation of a universal classifier. Each of the layers 174*a*-174*d* may be heterogenous. The DNN 170 may be configured to model complex, non-linear relationships. Intermediate layers, such as intermediate layer 174*c*, may provide compositions of features from lower layers, such as layers 174*a*, 174*b*, providing for modeling of complex data.

In some embodiments, the DNN 170 may be considered a stacked neural network including multiple layers each configured to execute one or more computations. The computation for a network with L hidden layers may be denoted as:

$$f(x) = f\left[a^{(L+1)}\left(h^{(L)}\left(a^{(L)}\left( \ldots \left(h^{(2)}\left(a^{(2)}\left(h^{(1)}\left(a^{(1)}(x)\right)\right)\right)\right)\right)\right)\right)\right]$$

where $a^{(l)}(x)$ is a preactivation function and $h^{(l)}x)$ is a hidden-layer activation function providing the output of each hidden layer. The preactivation function $a^{(l)}x)$ may include a linear operation with matrix $W^{(l)}$ and bias $b^{(l)}$ where:

$$a^{(l)}(x) = W^{(l)}x + b^{(l)}$$

In some embodiments, the DNN 170 is a feedforward network in which data flows from an input layer 172 to an output layer 176 without looping back through any layers. In some embodiments, the DNN 170 may include a backpropagation network in which the output of at least one hidden layer is provided, e.g., propagated, to a prior hidden layer. The DNN 170 may include any suitable neural network, such as a self-organizing neural network, a recurrent neural network, a convolutional neural network, a modular neural network, and/or any other suitable neural network.

In some embodiments, a DNN 170 may include a neural additive model (NAM). An NAM includes a linear combination of networks, each of which attends to (e.g., provides a calculation regarding) a single input feature. For example, a NAM may be represented as:

$$y = \beta + f_1(x_1) + f_2(x_2) + \ldots + f_K(x_K)$$

where β is an offset and each $f_i$ is parametrized by a neural network. In some embodiments, the DNN 170 may include a neural multiplicative model (NMM), including a multiplicative form for the NAM mode using a log transformation of the dependent variable y and the independent variable x:

$$y = e^{\beta} e^{f(\log x)} e^{\sum_i f_i^d(d_i)}$$

where d represents one or more features of the independent variable x.

Identification of one or more codes from a code library and corresponding supporting entities associated with code reviews, such as medical risk adjustment, can be burdensome and time consuming for users, especially when manual review of anthology documents must be performed by trained technical experts. Typically, a user must review the entirety of an anthology document 252 to identify codes and/or associated elements. Systems configured to provide automated encounter delineation and code identification, as disclosed herein, significantly reduce this problem, allowing users to locate relevant codes and the corresponding supporting portions of an anthology document 252 with fewer, or in some case no, active steps. For example, in some embodiments described herein, when a user is presented with an annotated anthology document, interface element, such as linkage elements 284*a*, 284*b* include, or is in the form of, a link to a corresponding value set data structure 264 and/or the components thereof. Each linkage element 284*a*, 284*b* thus serves as a programmatically generated navigational shortcut to corresponding portions of an anthology document 252, allowing a user to bypass the traditional navigation and review required for code reviews. Beneficially, programmatically identifying linkages between value set data structures 264 and specific entities within the annotated anthology document 252*a* may improve the speed of the user's navigation of the corresponding anthology document 252 through an electronic interface, rather than requiring the user to page through multiple other pages in order to locate the relevant entities.

It will be appreciated that delineation of individual encounter records, generation of value set data structure, and generation of an interface including linkage elements providing links between entities within an anthology document and elements of the value set data structure, as disclosed herein, particularly on large anthology documents associated with a medical domain, is only possible with the aid of computer-assisted machine-learning algorithms and techniques, such as the disclosed document processing engine, resource generation engine, value set generation engine, code linkage engine, etc. In some embodiments, machine learning processes including natural language processing are used to perform operations that cannot practically be performed by a human, either mentally or with assistance, such as automated entity identification and linkage within electronic documents.

Figure 14:
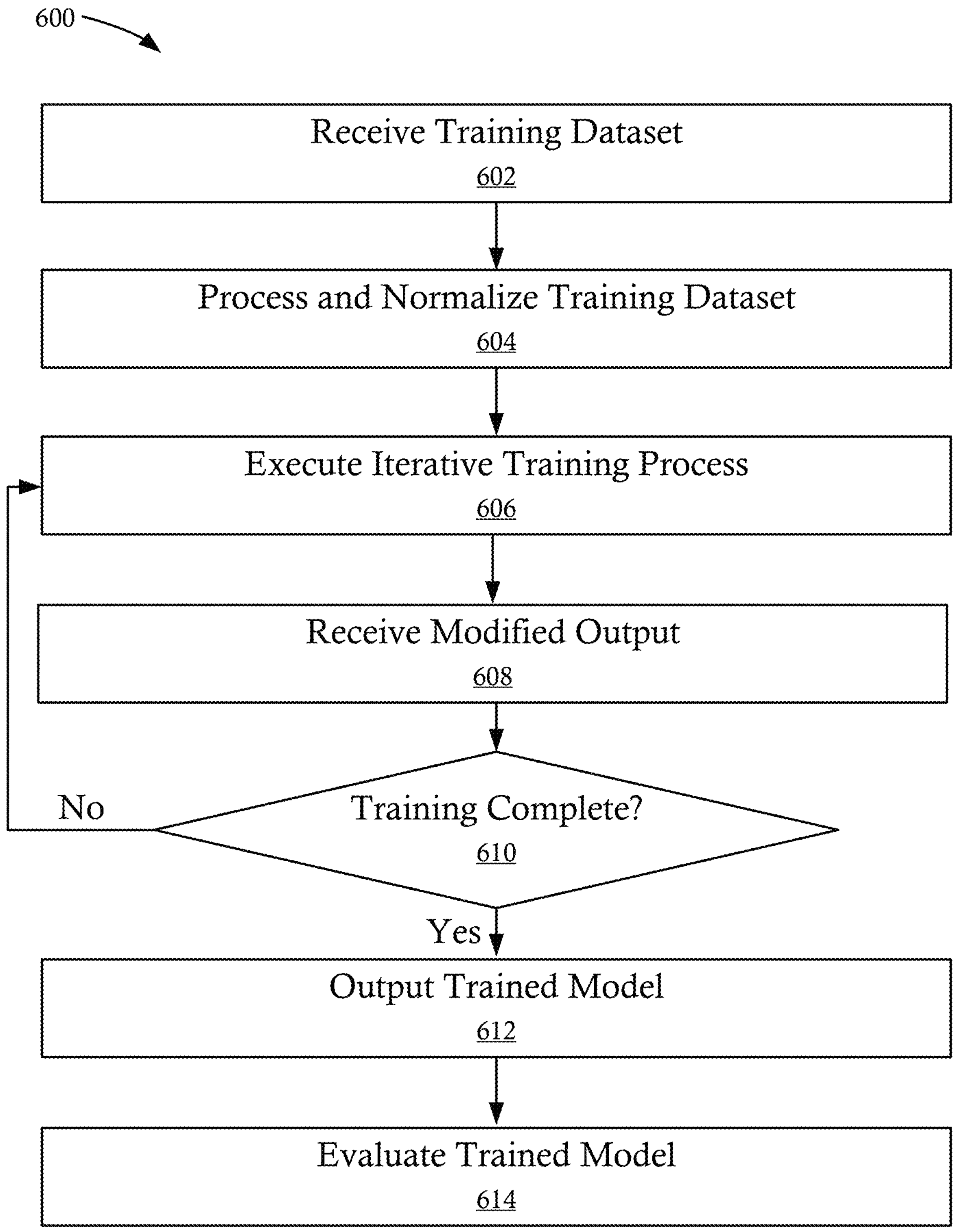
FIG. 14 is a flowchart illustrating a training method for generating a trained machine learning model, in accordance with some embodiments.
Figure 15:
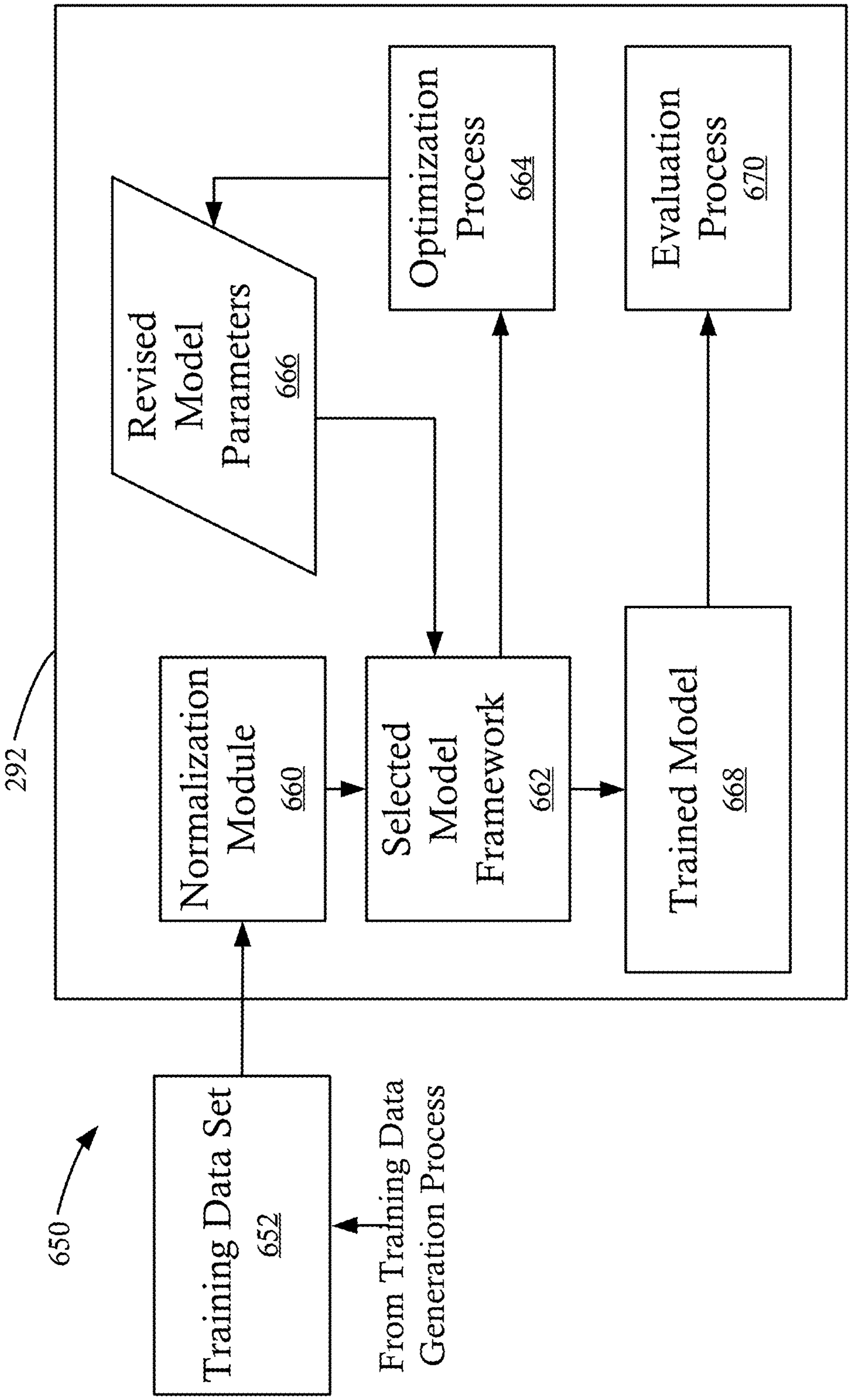
FIG. 15 is a process flow illustrating various steps of the training method of FIG. 14, in accordance with some embodiments.

In some embodiments, one or more engines, such as a document processing engine 254, can include and/or implement one or more trained models, such as a trained natural language processing model. In some embodiments, one or more trained models can be generated using an iterative training process based on a training dataset. FIG. 14 illustrates a method 600 for generating a trained model, such as a trained natural language processing model, in accordance with some embodiments. FIG. 15 is a process flow 650 illustrating various steps of the method 600 of generating a trained model, in accordance with some embodiments. At step 602, a training dataset 652 is received by a system, such as a processing device 10. The training dataset 652 can include labeled and/or unlabeled data.

At optional step 604, the received training dataset 652 is processed and/or normalized by a normalization. module 660. For example, in some embodiments, the training dataset 652 can be augmented by imputing or estimating missing values of one or more features associated with a natural language processing model. In some embodiments, processing of the received training dataset 652 includes outlier detection configured to remove data likely to skew training of a natural language processing model. In some embodiments, processing of the received training dataset 652 includes removing features that have limited value with respect to training of the natural language processing model.

At step 606, an iterative training process is executed to train a selected model framework 662. The selected model framework 662 can include an untrained (e.g., base) machine learning model, such as natural language processing framework and/or a partially or previously trained model (e.g., a prior version of a trained model). The training process is configured to iteratively adjust parameters (e.g., hyperparameters) of the selected model framework 662 to minimize a cost value (e.g., an output of a cost function) for the selected model framework 662. In some embodiments, the cost value is related to natural language processing model. As discussed above, the iterative training process may be implemented by, for example, a model generation engine 292.

The training process is an iterative process that generates set of revised model parameters 666 during each iteration. The set of revised model parameters 666 can be generated by applying an optimization process 664 to the cost function of the selected model framework 662. The optimization process 664 can be configured to reduce the cost value (e.g., reduce the output of the cost function) at each step by adjusting one or more parameters during each iteration of the training process.

After each iteration of the training process, at step 608, a determination is made whether the training process is complete. The determination at step 608 can be based on any suitable parameters. For example, in some embodiments, a training process can complete after a predetermined number of iterations. As another example, in some embodiments, a training process can complete when it is determined that the cost function of the selected model framework 662 has reached a minimum, such as a local minimum and/or a global minimum.

At step 610, a trained model 668, such as a trained natural language processing model, is output. At optional step 612, a trained model 668 can be evaluated by an evaluation process 670. A trained model can be evaluated based on any suitable metrics, such as, for example, an F or F1 score, normalized discounted cumulative gain (NDCG) of the model, mean reciprocal rank (MRR), mean average precision (MAP) score of the model, and/or any other suitable evaluation metrics. Although specific embodiments are discussed herein, it will be appreciated that any suitable set of evaluation metrics can be used to evaluate a trained model.

Although the subject matter has been described in terms of exemplary embodiments, it is not limited thereto. Rather, the appended claims should be construed broadly, to include other variants and embodiments, which may be made by those skilled in the art.

What is claimed is:

1. A system, comprising:

a non-transitory memory;

a processor communicatively coupled to the non-transitory memory, wherein the processor is configured to read a set of instructions to:

receive an anthology document associated with a domain;

implement a trained multimodal extraction model to identify one or more individual encounter records within the anthology document, wherein the trained multimodal extraction model is configured to receive at least two input types generated from the anthology document;

for each of the one or more individual encounter records:

generate one or more resource data structures representative of an entity in a selected one of the one or more individual encounter records, wherein the entity is identified by a trained natural language processing model;

generate one or more value set data structures comprising at least one of the one or more resource data structures, at least one code element comprising a code selected from a code library associated with the domain, and at least one linkage element representative of a linkage between the entity of the at least one of the one or more resource data structures and the code element, wherein:

each of the one or more value set data structures comprise a primary resource data structure and at least one secondary resource data structure, wherein the at least one linkage element is representative of a linkage between the entity of the primary resource data structure and the code element, and each of the one or more value set data structures and each of the one or more resource data structures include one of a plurality of types, and wherein the type of the value set data structure is determined by a type of the primary resource data structure; and generate instructions configured to display a user interface that includes recommended codes associated with the individual encounter records, the user interface comprising the anthology document, the code selected from the code library, and a visual element representative of the at least one linkage element, wherein the visual element representative of the at least one linkage element is user-selectable so as to associate the code selected from the code library with the individual encounter record.

2. The system of claim 1, wherein the multimodal extraction model is configured to receive image input data and text input data.

3. The system of claim 1, wherein the trained multimodal extraction model is configured to generate a page prediction for each page in the anthology document, and wherein the one or more individual encounter records are generated by a rules-based module based on the page prediction for each page in the anthology document.

4. The system of claim 1, comprising generating encounter metadata for each of the one or more individual encounter records.

5. The system of claim 1, wherein the one or more resource data structures each comprise one of a condition resource data structure, a medication resource data structure, an observation resource data structure, or a procedure resource data structure.

6. The system of claim 1, wherein each of the one or more resource data structures comprise an annotation data element, at least one context data element, and at least one metadata element.

7. The system of claim 6, wherein the entity of each of the one or more resource data structures is defined by the annotation data element.

8. The system of claim 6, wherein each of the one or more resource data structures are generated by a rules-based resource construction module based on the annotation data element, the at least one context data element, and the at least one metadata element.

9. A computer-implemented method, comprising:

receiving an anthology document associated with a domain;

implementing a trained multimodal extraction model to identify one or more individual encounter records within the anthology document;

for each of the one or more individual encounter records:

generating one or more resource data structures comprising an annotation data element representative of an entity in a selected one of the one or more individual encounter records, wherein the entity is identified by a trained natural language processing model;

generating one or more value set data structures comprising at least one of the one or more resource data structures, at least one code element comprising a code selected from a code library associated with the domain, and at least one linkage element representative of a linkage between the entity of the at least one of the one or more resource data structures and the code element, wherein:

each of the one or more value set data structures comprise a primary resource data structure and at least one secondary resource data structure, wherein the at least one linkage element is representative of a linkage between the entity of the primary resource data structure and the code element, and each of the one or more value set data structures and each of the one or more resource data structures include one of a plurality of types, and wherein the type of the value set data structure is determined by a type of the primary resource data structure; and generating instructions configured to display a user interface that includes recommended codes associated with the individual encounter records, the user interface comprising the anthology document, the code selected from the code library, and a visual element representative of the at least one linkage element, wherein the visual element representative of the at least one linkage element is user-selectable so as to associate the code selected from the code library with the individual encounter record.

10. The computer-implemented method of claim 9, wherein the multimodal extraction model is configured to receive image input data and text input data.

11. The computer-implemented method of claim 9, wherein the trained multimodal extraction model is configured to generate a page prediction for each page in the anthology document, and wherein the one or more individual encounter records are generated by a rules-based module based on the page prediction for each page in the anthology document.

12. The computer-implemented method of claim 9, wherein each of the one or more resource data structures comprise at least one context data element, at least one metadata element, or a combination thereof.

13. The computer-implemented method of claim 12, wherein each of the one or more resource data structures are generated by a rules-based resource construction module based on the annotation data element and the at least one context data element, at least one metadata element, or the combination thereof.

14. A non-transitory computer readable medium having instructions stored thereon, wherein the instructions, when executed by at least one processor, cause at least one device to perform operations comprising:

receiving an anthology document associated with a domain;

implementing a trained multimodal extraction model to identify one or more individual encounter records within the anthology document, wherein the trained multimodal extraction model is configured to receive a text input and an image input, wherein each of the text input and the image input are generated from the anthology document;

for each of the one or more individual encounter records:

generating one or more resource data structures comprising an annotation data element representative of an entity in a selected one of the one or more individual encounter records, wherein the entity is identified by a trained natural language processing model;

generating one or more value set data structures comprising at least one of the one or more resource data structures, at least one code element comprising a code selected from a code library associated with the domain, and at least one linkage element representative of a linkage between the entity of the at least one of the one or more resource data structures and the code element, wherein:

each of the one or more value set data structures comprise a primary resource data structure and at least one secondary resource data structure, wherein the at least one linkage element is representative of a linkage between the entity of the primary resource data structure and the code element, and each of the one or more value set data structures and each of the one or more resource data structures include one of a plurality of types, and wherein the type of the value set data structure is determined by a type of the primary resource data structure; and generating instructions configured to display a user interface that includes recommended codes associated with the individual encounter records, the user interface comprising the anthology document, the code selected from the code library, and a visual element representative of the at least one linkage element, wherein the visual element representative of the at least one linkage element is user-selectable so as to associate the code selected from the code library with the individual encounter record.

15. The non-transitory computer readable medium of claim 14, wherein the trained multimodal extraction model is configured to generate a page prediction for each page in the anthology document, and wherein the one or more individual encounter records are generated by a rules-based module based on the page prediction for each page in the anthology document.

16. The non-transitory computer readable medium of claim 14, wherein each of the one or more resource data structures comprise at least one context data element, at least one metadata element, or a combination thereof, and wherein each of the one or more resource data structures are generated by a rules-based resource construction module based on the annotation data element and the at least one context data element, at least one metadata element, or the combination thereof.

* * * * *